(12) United States Patent
Hartman et al.

(10) Patent No.: US 11,776,659 B1
(45) Date of Patent: Oct. 3, 2023

(54) SIMULATIONS NETWORKED ACTIVITY USING DYNAMICS-BASED CONSTRAINTS ON REUSABLE NETWORK COMPONENT

(71) Applicant: X DEVELOPMENT LLC, Mountain View, CA (US)

(72) Inventors: Jana Hartman, Sunnyvale, CA (US); Frank Russo, Sunnyvale, CA (US)

(73) Assignee: X Development LLC, Mountain View, CA (US)

( * ) Notice: Subject to any disclaimer, the term of this patent is extended or adjusted under 35 U.S.C. 154(b) by 1,142 days.

(21) Appl. No.: 16/443,968

(22) Filed: Jun. 18, 2019

(51) Int. Cl.
*G16B 5/30* (2019.01)

(52) U.S. Cl.
CPC .................................. *G16B 5/30* (2019.02)

(58) Field of Classification Search
None
See application file for complete search history.

(56) References Cited

OTHER PUBLICATIONS

Gevorgyan, Albert, et al. "SurreyFBA: a command line tool and graphics user interface for constraint-based modeling of genome-scale metabolic reaction networks." Bioinformatics 27.3 (2011): 433-434.*

* cited by examiner

*Primary Examiner* — G Steven Vanni
(74) *Attorney, Agent, or Firm* — Kilpatrick Townsend & Stockton LLP

(57) ABSTRACT

Techniques for simulating networks using dynamics-based constraints are disclosed.

26 Claims, 11 Drawing Sheets

SIMULATIONS NETWORKED ACTIVITY USING DYNAMICS-BASED CONSTRAINTS ON REUSABLE NETWORK COMPONENT

FIELD

Methods and systems disclosed herein relate generally to generating dynamics-based constraints on activity of reusable network components in network simulations.

BACKGROUND

The development of accurate simulations and models can facilitate generation of testable and focused hypotheses. Some simulations of systems are constructed based on bottom-up knowledge. Specifically, the activity and interaction of particular low-level components may be known in some contexts, and the simulation may be generated to replicate these low-level activities and interactions. When such low-level operation can be simulated for many components, high-level activity of a network of the components can be simulated. Some simulations are constructed using a top-down configuration. Specifically, a simulation can be constructed to perform in accordance with high-level activity with more flexibility afforded to low-level components.

One value of simulations is to be able to generate predictions as to how a given new set of inputs or simulation alterations would affect operation (e.g., output and/or activity) of the overall system and/or of individual components of the system. This information can be used to determine how to respond to a given system state by further adjusting the system in a particular manner to maintain high performance of the system.

The value of the simulations may be particularly high for biological simulations. For example, the simulation may be used to identify how a given biological deficit may cascade to affect other processes. Identifying a therapeutic to target one of these downstream effects may be an effective treatment option. However, such use cases rely upon simulations that accurately model low-level component function, high-level activity, dynamics across levels, and component interactions.

SUMMARY

In some embodiments, a computer-implemented method is provided. A set of reactions representative of activity of a biological network is identified. Each reaction identifying stoichiometry is indicative of relative quantities of metabolites being consumed and produced by the reaction. Based on the set of reactions, a metabolite is identified that is reused across cycles of at least one reaction. A constraint on a quantity of the metabolite is defined based on one or more characteristics of the reuse of the metabolite across cycles of the at least one reaction. A simulation is executed using the set of reactions and the constraint. Execution of the simulation generates one or more simulation outputs.

In some instances, the method further includes identifying a use rate indicative of a quantity of the cycles of the at least one reaction performed per unit of time; and identifying a per-cycle duration of the at least one reaction; where the one or more characteristics of the reuse of the metabolite include the use rate and the per-cycle duration. In some instances, the at least one reaction includes a set of reactions, where a first reaction of the set of reactions consumes the metabolite, and a later reaction of the set of reactions releases the metabolite. In some instances, the method further includes determining that the metabolite is further reused across other cycles of another at least one reaction; where the constraint on the quantity of the metabolite is defined further based on one or more other characteristics of the reuse of the metabolite across other cycles of the other at least one reaction. In some instances, the constraint is defined to indicate that the quantity of the metabolite is to remain to be at least equal to a sum of multiple product values, the multiple product values including: a first product of a first use rate and a first duration corresponding to the at least one reaction; and a second product of a second use rate and a second duration corresponding to the other at least one reaction. In some instances, the biological network is a cell, and the metabolite is a cofactor, enzyme or ribosome. In some instances, executing the simulation includes identifying, for each reaction of the set of reactions, a flux of the reaction based on an objective function that is defined based on the stoichiometries of the set of reactions. In some instances, the one or more simulation outputs include time-course data indicating dynamics of at least part of the network. In some instances, executing the simulation includes using linear programming.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

Figure 1:
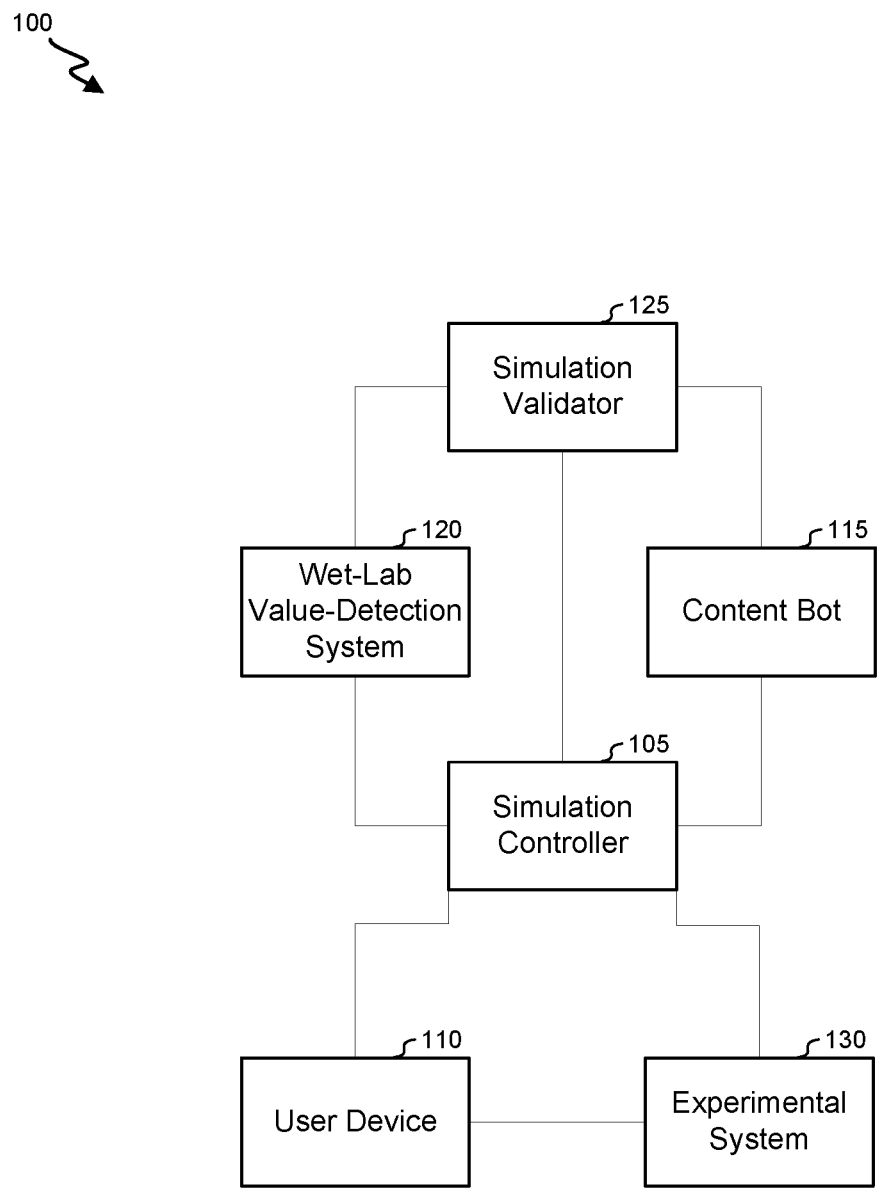
FIG. 1 shows an interaction system for configuring and using a simulation to facilitate subsequent experiment configurations according to some embodiments of the invention.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

In some instances, techniques are disclosed for simulating activity within a network. For example, the simulation may simulate reactions occurring within a cell. The simulation may use (for example) mechanistic-based models, structural models, constraint-based models and/or reaction-based models. In some instances, the cell is represented by one or more modules, and a model (e.g., representing one or more reactions) is assigned to each module. At each time step, for each module, input data (e.g., identifying levels of various metabolites) is retrieved and processed by the assigned model to produce output data. At least part of the input data may be retrieved from a cross-module data structure. Corresponding elements of the output data can be synthesized across modules and used to update the cross-module data structure. Thus, the simulation can be used to determine how metabolite levels and reaction prevalence change in time given a particular cell configuration. For example, the simulation can be used to determine how a particular mutation affects a growth rate of a cell and which reactions and/or metabolites are constraining the growth.

In some instances, a model that is used in the simulation (e.g., across the entire simulation or for one or more modules) is configured to balance compounds, such that a quantity of each given compound that is consumed by a set of reactions is equal to a quantity of the given compound that is produced by the set of reactions. Each reaction may have fixed stoichiometry, such that the simulation is configured to secure this balance by identifying relative ratios and/or fluxes at which the reactions are performed.

However, when a compound is recycled instead of being consumed, a simulation may detect the non-consumed compound as being consistently balanced regardless of a flux of the corresponding reaction(s). Thus, a simulation may (for example) produce a solution that would require more of these non-consumed compounds than were available, which could lead to unphysiological results.

One approach to address this issue is to add a constraint that constrains a level of a consumed compound or a flux of a reaction based on a level of the non-consumed compound. However, in this instance, if the constraint limits an objective of the simulation, the limit would be ascribed to a limit of the non-consumed compound. This may not accurately represent the physiological circumstances that actually limit the objective. For example, suppose that an objective is set to maximize growth and that a reaction is defined that requires a non-consumed compound and that transforms a reactant compound to a product compound required for growth. Further consider a constraint that is defined that prevents performance of the reaction or that limits a quantity of the reactant compound when the non-consumed compound is absent or limited. Results of the simulation may then indicate that growth was stunted as a result of the non-consumed compound be absent or of low levels, rather than indicating that the growth was stunted as a result of the product compound being absent or present at low levels.

In some embodiments, a simulation is configured that includes a constraint that relates a level of the non-consumed compound to dynamics of the reaction or series of reactions that require the non-consumed compound. The dynamics pertain both to a flux of the reaction or series of reactions indicating a rate at which the reaction or series of reactions is simulated as occurring and a duration of part or all of the reaction or series of reactions. For example, the duration may include a duration of a full reaction or full series of reactions or a part thereof that involves the non-consumed compound. That is, the duration may correspond to a sequestration duration during which a given iteration of a reaction or series of reactions is using the non-consumed compound such that it is unavailable to be used in another iteration of the reaction or series of reactions.

While a given non-consumed compound may be repeatedly used across different iterations of a reaction or series of reactions, sequestration durations limit this repeated use. For example, if a sequestration duration was half of a time-step duration, the non-consumed compound could contribute to, at most, two reactions or series of reactions per time step. Thus, simulating performance of ten iterations of the reaction or series of reactions per time step would require a presence of at least ten non-consumed compounds. Thus, the constraint can require that an availability, quantity or count of the non-consumed compound be greater than or equal to a product of the sequestration duration and a flux of the associated reaction or series of reactions that indicates a quantity of the reaction or series of reactions occurring per unit time.

In some instances, a non-consumed compound may be used in multiple types of reactions and/or series of reactions. An availability of the non-consumed compound may then be affected by sequestration durations of the multiple types of reactions and/or series of reactions and on the fluxes of the multiple types of reactions and/or series of reactions. Accordingly, a constraint may be applied that indicates that an availability, quantity or count of the non-consumed compound is to be greater than or equal to a sum of reaction-specific or reaction-series-specific products of a respective sequestration duration and flux.

In some instances, the constraint is implemented as a hard constraint, such that each solution that is identified by the simulation is required to and necessarily conforms with the constraint. Thus, if execution of the simulation does not identify any solution that conforms with the constraint (and each other constraint), the simulation terminates (e.g., reflecting cell death). In some instances, rather than enforcing the above-defined relative equation as a constraint.

FIG. 1 shows an interaction system 100 for configuring instances or versions of a model and using a simulation to facilitate subsequent experiment configurations (e.g., simulation of a biological system's response to a new demand) according to various embodiments. Each instance of the models may have a combination of modules, perturbations (such as knockouts), and may be built using a particular set of experimental data. In order to facilitate the configuring of a model (e.g., a biological system) and simulate an outcome of the model, the interaction system 100 can include one or more components, each of which can include (for example) one or more servers, one or more computers and/or one or more mobile devices. In some instances, two or more of the components can be included in a same server, same server system, same computer, etc. Interaction system 100 can include one or more networks (e.g., a wired network, a wireless network, the Internet, a local area network, a wide area network, a short-range network, etc.), such that each component in the interaction system 100 can communicate with one or more other components in the interaction system 100.

Interaction system 100 can include a simulation controller 105 that defines, generates, updates and/or executes each of one or more simulations. A simulation can be configured to simulate dynamic progression through states, a time-evolved state of a model of a biological system and/or a steady state based on an iterative module-based assessment. It will be appreciated that identifying a steady-state and/or balanced solution for a module at a given time step need not indicate that a steady-state and/or balanced solution has been, can be or will be identified for the model in general (e.g., as metabolites produced and/or consumed at one module may further be produced and/or consumed at another module that need not be configured for balancing fluxes).

A given model can be used to generate and run any number of simulations. Differing initial conditions and/or differing automatically generated values in stochastic portions of the simulation (e.g., generated using a pseudo-random number generation technique, a stochastic pull from a distribution, etc.) can result in different output results of different simulations. The biological system model can be made up of one or more modules, and during a simulation run, each module is run independently and passes results back up to the biological system model level. More specifically, the biological system (e.g., a whole cell) may be modeled in accordance with a coordinated operation of multiple modules that represent structure(s) and/or function(s) of the biological system. Each module may be defined to execute independently, except that a shared set of state values (e.g., a state vector) maintained at the biological system model level may be used and accessed by multiple modules at each time point.

In some instances, each module of the biological system is configured to advance across iterations (e.g., time points) using one or more physiological and/or physics-based models (e.g., flux balance analysis (FBA), template synthesis, bulk-mass flow analysis, constant non-specific degradation, empirical analysis, etc.). The module-specific iteration processing can further be based on one or more module-specific state values (as determined based on an initial definition for an initial iteration processing or a result of a previous iteration processing for a subsequent iteration processing). The module-specific iteration processing can further be based on one or more parameters defined for the module that are fixed and/or static across iterations across iterations.

Simulation controller 105 can generate simulation configurations using one or more inputs received from a user device 110. For example, simulation controller 105 may generate an interface (or may at least partly define specifications for an interface) that is to be availed and/or transmitted to user device 110 and to include input fields configured to receive inputs that correspond to a selection of (for example) one or more modules to be used for a given biological system model, a model type to be used for each of the one or more modules, one or more parameters that are to be effected by a given module's model and used during execution, and/or one or more initial state-value definitions that are to be used by a given module's model and used during execution. In some instances, the interface identifies a default value for each of one, more or all parameters of the model and for each of one, more or all of the initial-state values of the model and is configured to receive a modification to a subset or all of the parameters and/or initial-state values for which a default value was identified. In some instances, modifying a default initial-state value and/or parameter can correspond to a perturbation of performance of a corresponding module and/or the biological system.

Figure 2:
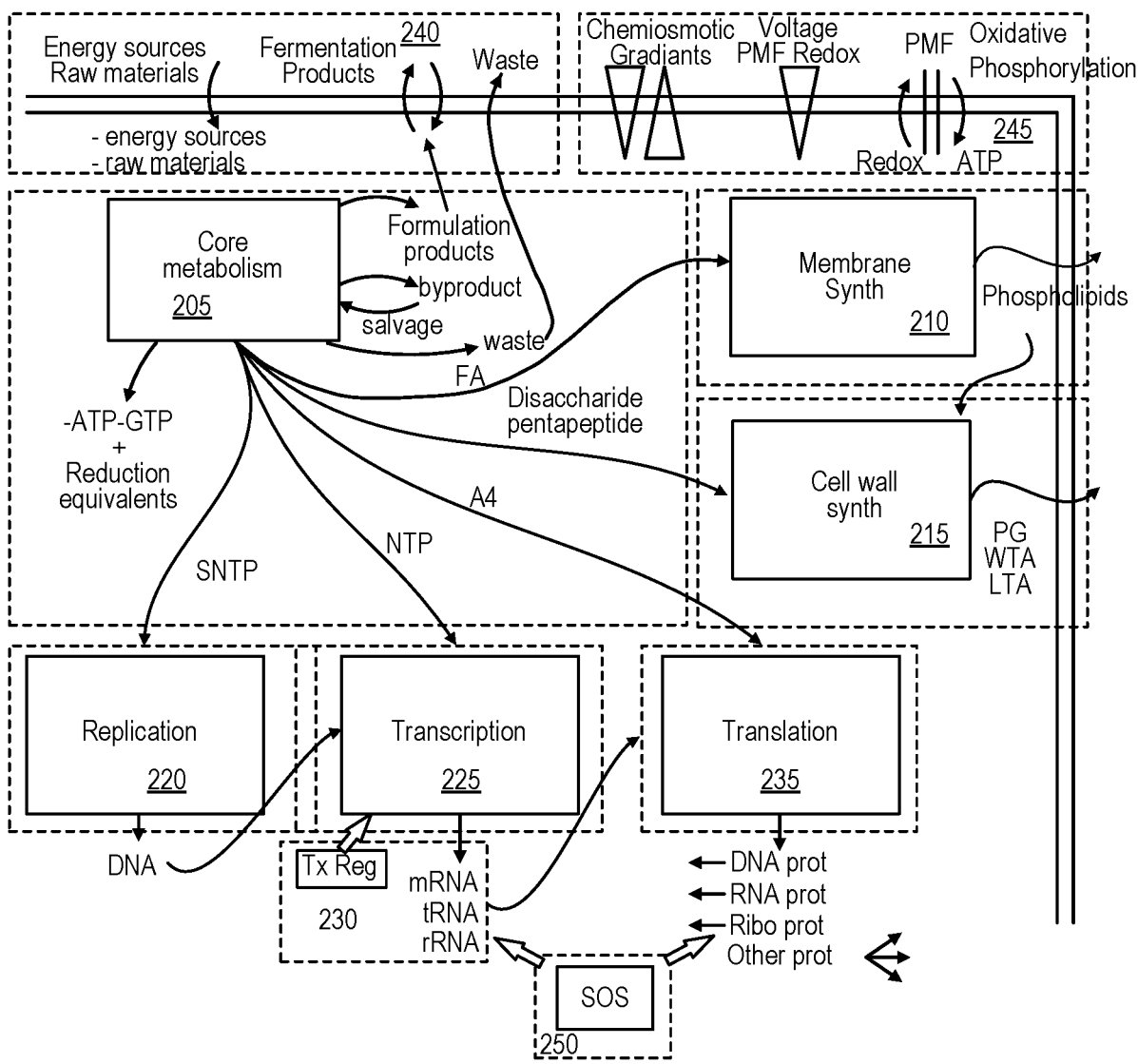
FIG. 2 shows a representation of modules representing distinct biological functions according to an embodiment of the invention.

As another example, the interface may further or alternatively be configured to receive an input that corresponds to a selection of one or more default modules and a selection of a model type to be used for each of one or more modules. For example, the interface may include one or more modules (as shown in FIG. 2) representing distinct biological functions in a biological system model, and for each module: a name of the module, a default model type for the module and an option configured to receive a selection of another model type for the module (e.g., that identifies one or more other model types that can be selected for the module).

Default structure of a simulation (e.g., corresponding to default modules, default parameters, default initial-state values and/or default model selections) can be determined based on detected internal or external content and/or based on lab results (e.g., results from physical experiments). The content can include (for example) online, remote and/or local content that is collected by a content bot 115. Content bot 115 can (for example) include a crawler that performs a focused crawling and/or focused browsing (for example) the Internet, a part of the Internet, one or more pre-identified websites, a remote (e.g., cloud-based) storage system, a part of a remote storage system, a local storage system and/or a part of a local storage system. The crawling can be performed in accordance with one or more crawling policies and/or one or more queries that corresponds to one or more modules and/or models (e.g., where each query includes a variable name, representation or description and/or a cellular-function name, .representation or description).

The lab results can be received from a wet-lab value detection system 120, which can be configured to trigger performance of one or more investigations (e.g., physical experiments) to detect and/or measure data corresponding to an initial-state value and/or data corresponding to a characteristic or parameter of a biological system. Wet-lab value-detection system 120 can transmit one or more results of the investigation(s) back to simulation controller 105, which may thereafter determine and/or define a default initial-state value or parameter or a possible modification thereof based on the result(s).

Interaction system 100 further includes a simulation validator 125, which can be configured to validate performance of a simulation. The validation may be performed based on pre-identified indications as to how a biological system functions normally and/or given one or more perturbations. Such indications can be defined based on content collected from content bot 115 and/or results from wet-lab value-detection system 120. The data used to validate the simulation may include (for example) one or more balanced values, one or more values indicative of cell dynamics, one or more steady-state values, one or more intermediate values and/or one or more time-course statistics. Simulation validator 125 may return a performance result that includes (for example) a number, category, cluster or binary indicator to simulation controller 105. Simulation controller 105 may use the result to determine (for example) whether a given simulation configuration is suitable for use (e.g., in which case it may be selectable in an interface).

After a simulation is configured with definitions and/or selections of modules, module-specific models, parameters and/or initial-state values, simulation controller 105 can execute the simulation (e.g., in response to receiving an instruction from user device 110 to execute the simulation). The simulation execution can produce one or more simulation results, which may include (for example) one or more balanced values, kinetic values, etc. For example, the simulation can identify a solution for a set of reaction-corresponding stoichiometric equations using linear algebra, such that production and consumption of metabolites represented in the equations is balanced. Notably, this balance may be specific to a given module and need not be achieved for all metabolites produced or consumed by reactions for a given module (e.g., as a non-zero net production or consumption of one or more boundary metabolites may be predefined and/or a target result for a module). Simulation controller 105 can transmit the results (e.g., via an interface) to user device 110.

In some instances, the results can be used to trigger and/or define a subsequent experiment. For example, simulation controller 105 may determine whether a given predefined condition is satisfied based on the results and, if so, may transmit simulation-specific data (e.g., indicating one or more initial-state values, parameters, mutations corresponding to simulation definitions, etc.) to an experimental system 130. The transmission may be indicative of and/or include an instruction to perform an experiment that corresponds to the simulation.

As another example, upon receiving simulation results from simulation controller 105, user device 110 can present an interface that includes some or all of the results and an input component configured to receive input corresponding to an instruction to perform an experiment that corresponds to the simulation. Upon receiving a selection at the input component, user device 110 may transmit data corresponding to the simulation to experimental system 130. After performing a requested experiment, experimental system 130 may return one or more results to simulation controller 105 and/or user device 110.

FIG. 2 shows an illustrative representation of given biological system model 200. The overall modeling strategy includes partitioning the biological system model 200 into modules that can be modeled separately, using a methodology and level of detail appropriate to and/or selected for each module. The partitioning and level of detail for each module can be selected based on (for example) the experiments or simulations that are to be run by the model (e.g., the questions trying to be solved by the model). The selection may be made by the modeler and/or computing system (e.g., the interaction system 100 described with respect to FIG. 1). For example, a user working through an interface of an integrated development environment, a script, and/or an automated system may be implemented to select one or more modules and select a model type to be used for each of one or more modules to ultimately generate the biological system model 200. Additionally or alternatively, the partitioning can be customized and depend on an assessment of the biological functions defined for the initial high-level data set. For example, a separate module may be defined to represent each of the following biological functions: core metabolism 205, membrane synthesis 210, cell-wall synthesis 215, DNA replication 220, transcription 225, transcription regulation 230, translation 235, RNA salvage (not shown), protein and RNA maturation, protein salvage (not shown), transmembrane transport 240 (including electron chain, oxidative phosphorylation, redox, and pH interconversion activity 245), signal transduction (not shown), stress response and growth rate regulation 250, cell division, chemotaxis (not shown), and cell-cell signaling (not shown).

Biological system model 200 can include at least one module that handles core metabolism 205. One possible core metabolic module uses an FBA model, which takes its general shape from standalone FBA, but includes modifications that account for interactions of the core metabolic module with other modules. Each of one, more or all other modules may have their own production and consumption of some of the same molecules within the FBA network, as described in further detail herein. However, as should be understood to those of ordinary skill in the art, an FBA model does not have to be incorporated into the overall biological system model 200 in order for every simulation to work. Instead, various types of models can be used for the modules (e.g., core metabolism 205, membrane synthesis 210, cell-wall synthesis 215, etc.) so long as the type of models can be configured to read values from the state vector and return a list of changes that should be made to the state vector.

For one exemplary instantiation of biological system model 200, core metabolism 205, membrane synthesis 210, and cell-wall synthesis 215 may be encompassed as a single FBA problem, whereas DNA replication 220, transcription 225, transcription regulation 230, and translation 235 may be isolated from the rest of the metabolic network. Meanwhile, transcription 225 and translation 235 may use a template synthesis model, and DNA replication 220 may use a bulk mass-flow model. Transcription regulation 230 may be empirical and static. Optionally, RNA salvage may be modeled using constant non-specific degradation, polymerized DNA, RNA, and protein levels may be determined by the intrinsic rates of the processes that produce them, and the remainder of the components are provided as inputs or parameters of the model.

For another exemplary instantiation of biological system model 200, core metabolism 205 may be encompassed as a single FBA problem. The balance of internal metabolite pools and the supply of building blocks for other processes may be maintained by core metabolism 205. DNA replication 220, transcription 225, transcription regulation 230, and translation 235 may then be isolated from the rest of the metabolic network. Membrane biosynthesis 210 and cell-wall synthesis 215 may be modeled by substrate- and catalyst-driven kinetics. Import and export rates and all exchange with the environment may be driven by the kinetics of membrane transport. Transcription 225 and translation 235 may use a template synthesis model, and DNA replication 220 may use a bulk mass-flow model. Transcription regulation 230 may be empirical and static. Optionally, RNA salvage may be modeled using representations of constant non-specific degradation, while polymerized DNA, RNA, and protein levels may be determined by the intrinsic rates of the processes that produce them, and the remainder of the components for the biological system can be provided as inputs or parameters of the model.

For another exemplary instantiation of biological system model 200, core metabolism 205 may be encompassed as an FBA problem, whereas one or more of membrane synthesis 210, cell-wall synthesis 215, DNA replication 220, transcription 225, transcription regulation 230, and translation 235 can be isolated from the rest of the metabolic network. The balance of internal metabolite pools and the supply of building blocks for other processes may be maintained by core metabolism 205. Membrane biosynthesis 210 and cell-wall synthesis 215 may be modeled by substrate and catalyst driven kinetics. Import and export rates, and all exchange with the environment may be driven by the kinetics of membrane transport. Redox balance, pH, and chemiosmotic gradients may be maintained explicitly. DNA replication 220, transcription 225 and translation 235 may use models based on initiation, elongation, and termination, Transcription regulation 230 may be pattern driven. Stress response and growth rate regulation 250 may be modeled using feedback control mechanisms. Optionally, RNA salvage may be modeled using constant non-specific degradation, while polymerized DNA, RNA, and protein levels may be determined by the intrinsic rates of the processes that produce them, and the remainder of the components for the biological system can be provided as inputs or parameters of the model.

While the biological system model 200 has been described at some length and with some particularity with respect to several described modules, combinations of modules, and simulation techniques, it is not intended that the biological system model 200 be limited to any such particular module configuration or particular embodiment. Instead, it should be understood that the described embodiments are provided as examples of modules, combinations of modules, and simulation techniques, and the modules, combinations of modules, and simulation techniques are to be construed with the broadest sense to include variations of modules, combinations of modules, and simulation techniques listed above, as well as other modules, combinations of modules, and simulation techniques configurations that could be constructed using a methodology and level of detail appropriate to each module and the biological system model 200.

Figure 3:
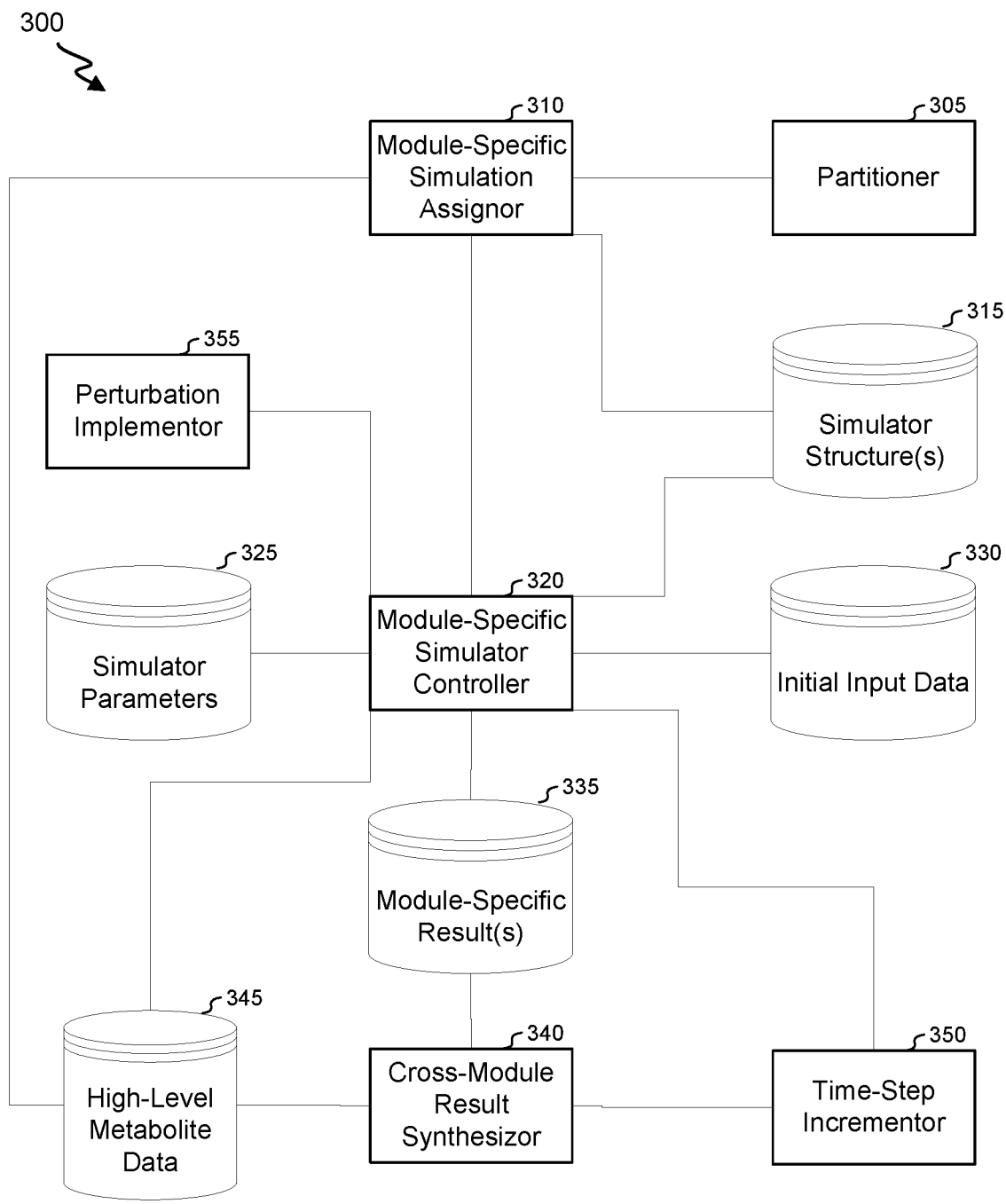
FIG. 3 shows a simulation controller that dynamically integrates results generated by different types of models to simulate higher-level states and reactions according to some embodiments of the invention.

FIG. 3 shows a simulation controller 300 that dynamically integrates results generated by different types of models configured by an integrated development environment (e.g., the interaction system 100 described with respect to FIG. 1) to simulate higher-level states and reactions of a biological system model (e.g., biological system model 200 as described with respect to FIG. 2) according to various embodiments. A partitioner 305 that can identify one or more modules to potentially use for a simulation. In some instances, the modules are identified to correspond to distinct biological functions or physiological processes within a biological system model. Nonetheless, at least one module (e.g., a core module) may address in more detail or cover a larger set of biological functions (e.g., correspond to a core level of physiology across the biological system such as general metabolism of the biological system), whereas at least one other module (e.g., a non-core module) may address in less detail or cover a smaller set biological function (e.g., correspond to transcription and/or translation).

A module-specific simulation assignor 310 may assign, to each module, a simulation type. The simulation type can be selected from amongst one or more types that are associated with the module and/or corresponding physiological process. The one or more types may differ with regard to (for example) a degree of detail to which a physiological process is modeled and/or how the process is modeled. For example, the one or more types may include a simulation using a metabolism-integrated model (e.g., in which specific end products are added to an objective function of a metabolism-based model), substrate- and/or catalyst-drive model using kinetic parameters and reactions, and/or higher-order structure model. A structure for each simulation type (e.g., that indicates how the simulation is to be performed and/or program code) is included in a simulator structure data store 315. Simulator structure data store 315 can further store an association between each simulation type and one or more modules for which the simulation type is associated and is permitted for selection for use.

A module-specific simulator controller 320 can identify, for each module, one or more simulation parameters and an input data set. The simulation parameters may be retrieved from a local data store (e.g., a simulator parameters data store 325) or from a remote source. Each of one or more of the simulation parameters may have been identified based on (for example) user input, a data-fitting technique and/or remote content. The parameter(s), once selected, may be fixed across time-step iterations.

At an initial time step, the input data set can include one or more initial input values, which may be retrieved from a local data store (e.g., an initial input data store 330) or from a remote source. Each of one or more of the initial input values may have been identified based on (for example) user input, a data-fitting technique and/or remote content. With respect to each subsequent time step, the input data set can include (for example) one or more results from a previous iteration of the module and/or one or more high-level results (e.g., cumulative or integrated results) generated from a previous iteration of the multi-module simulation. For example, a module-specific results data store 335 may store each of one, more or all results generated by the assigned simulation for each of one, more or all past time steps, and at least one of the stored results associated with a preceding time step (e.g., most recent time step) can be retrieved.

Upon identifying the input data set and parameters, module-specific simulator controller 320 can run the simulation assigned to the module. Execution of module-specific simulations may be performed concurrently, in parallel and/or using different resources (e.g., different processors, different memory and/or different devices). Results of the simulation run can be stored in module-specific results data store 335.

After results have been generated for each module, a cross-module result synthesizor 340 can access the module-specific results (from one or more module-specific results data stores or direct data availing) and synthesize the results to update high-level data such as a state vector (e.g., stored in a high-level metabolite data store 345). For example, a set of results generated by different modules but relating to a same variable may be identified. The results may be integrated by (for example) summing variable changes as indicated across the results (e.g., potentially with the implementation of one or more caps pertaining to a summed change or to a value of a variable after the summed change is effected). In some instances, a hierarchy is used, such that a result from one module (if available or if another condition is met) is to be exclusively used and a result from another module is to otherwise be used.

Upon synthesizing the results, a time-step incrementor 350 can increment a time step to a next time step so long as the simulation has not completed. It may be determined that the simulation is complete when (for example) processing for a predefined number of time steps has been performed, a particular result is detected (e.g., indicating that a target cell growth has occurred or that a cell has died) or steady state has been reached (e.g., as indicated by values for one or more predefined types of results differing by less than a predefined threshold amount across time steps). When the time step is incremented, module-specific simulator controller 320 can, for each module, collect a new input data set and run the assigned simulation. When the simulation is complete, an output can be generated to include one or more module-specific results, some or all high-level data and/or processed versions thereof. For example, the output may include time-course data for each of one or more metabolites, growth of the biological system over a time period (e.g., as identified by a ratio of availability values of one or more particular metabolites at a final time step as compared to availability values at an initial time step) and/or a growth rate. The output can be transmitted to another device (e.g., to be presented using a browser or other application) and/or presented locally.

Multi-module simulation controller 300 can also include a perturbation implementor 355. Perturbation implementor 355 can facilitate presentation of an interface on a user device. The interface can identify various types of perturbations (e.g., mutations). Perturbation implementor 355 may facilitate the presentation by transmitting data (e.g., HTTP data) to a user device, such that the interface can be presented online. Perturbation implementor 355 can detect a selection that corresponds to a particular perturbation and can send an indication to module-specific simulator controller 320. Module-specific simulator controller 320 can use functional gene data to determine how the mutation affects one or more metabolites and/or one or more simulated processes. A structure of a simulator, one or more simulator parameters and/or one or more initial-input values may then be adjusted in accordance was the perturbation's effects. Thus, multi-module simulation controller 300 can generate output that is indicative of how the perturbation affects (for example) physiological processes and/or growth of the biological system.

Figure 4:
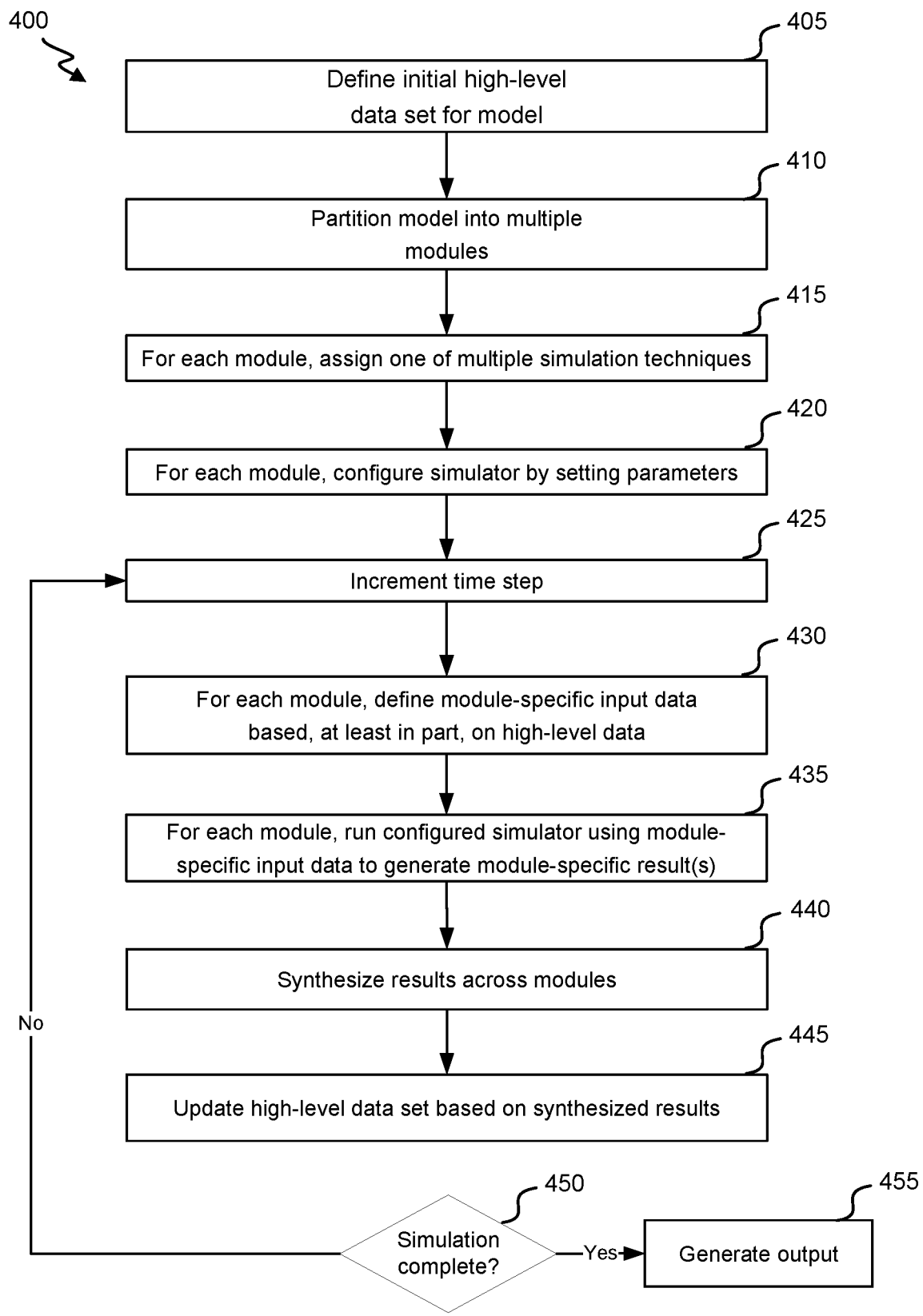
FIG. 4 shows a process for dynamically synthesizing results generated by multiple simulators to simulate higher-level results according to an embodiment of the invention.

FIG. 4 shows a process 400 for dynamically synthesizing results generated by multiple simulators to simulate higher-level results according to various embodiments. In some embodiments, the processes depicted in process 400 are implemented by the interaction system 100 of FIG. 1, and discussed with respect to the simulation controller 300 of FIG. 4. Process 400 begins at block 405 at which an initial high-level data set is defined for a biological system model. The initial high-level data set can identify (for example) variables, which may be referred to as the state of the biological system model or the state of the simulation, and these variables may be structured as a data structure (e.g., a state vector) and updated throughout a simulation run. In some instances, the variables include an initial availability of each of a set of molecules such as metabolites. The initial availability may be defined based on (for example) a default value, user input, data extracted from content (e.g., online content, remote content or local content that pertains to the molecules), etc. In some instances, the initial availability is determined based on whether any perturbation was identified (e.g., via user input) for a given simulation. If a perturbation was identified, the initial availability may be determined based on a particular perturbation that was identified and by using (for example) a look-up table to determine for which molecule(s) the perturbation affects an availability value and characteristics of such effect.

At block 410, a biological system model (e.g., a whole cell model) is partitioned into multiple modules. The partitioning can depend on metabolite dependencies and/or biological-functioning assessment. For example, a separate module may be defined to represent each of the following biological functions: core metabolism, membrane synthesis, cell-wall synthesis, DNA replication, transcription, transcription regulation, translation, RNA salvage, protein and RNA maturation, protein salvage, transmembrane transport (including electron chain, oxidative phosphorylation, redox, and pH interconversion activity), signal transduction, stress response and growth rate regulation (SOS), cell division, chemotaxis, and cell-cell signaling, as discussed in further detail with respect to FIG. 2. In some instances, two or more of these functions may be represented in a core module that models cell composition and growth using a single model. Particular cellular functioning need not be explicitly modeled and instead dynamics of end products of the particular cellular functioning may be modeled. For example, a core module may use a flux-based analysis or a simulation technique as described herein (e.g., in relation to FIG. 5 or FIG. 6).

In some instances, the partitioning may be performed based on user input and/or one or more default configurations. For example, an interface may be presented that identifies each potential separate module (e.g., an interface may be presented via simulation controller 105 as described with respect to FIG. 1). A default configuration may be to integrate the module into a core module (e.g., a core metabolism module) unless a contrary input is received or to perform a simulation using modeling specific to the module unless a contrary input is received. For example, an interface may be configured to receive one or more selections of modules that are to be excluded from a core module and to then integrate each other module into the core module.

At block 415, for each module, one or more simulation techniques are assigned to the module. A simulation technique may include a model type. In some instances, a simulation technique that is assigned to a core module includes a flux-based analysis or other simulation technique, as described herein. In some instances, a simulation technique includes a mechanistic model, a kinetic model, a partial kinetic model, a substrate- and/or catalyst-driven model, and/or a structural model. The simulation technique may be assigned based on (for example) user input and/or one or more predefined default selections. For example, for each non-core module, a default selection may be predefined that represents particular functioning of the module, and for each core module, a default selection may be predefined that simulates dynamics of metabolites across a simulated time period. An interface may identify, for each module, the default selection along with one or more other simulation techniques that are associated with the module (e.g., with the association(s) being based on stored data and/or a predefined configuration). User input may then indicate that an alternative simulation technique is to be used for one or more modules.

At block 420, for each module, a simulator is configured by setting parameters and variables. The parameters (e.g., numeric values) may correspond to inputs to be used in the simulation technique assigned to the module and that are not changed across time steps of the simulation. The particular parameters may be determined based on (for example) stored data, content, a communication from another system and/or user input. The one or more module-specific or cross-module variables (e.g., identifying an initial availability of one or more metabolites) may correspond to inputs to be used in the simulation technique assigned to the module and may be changed across time steps of the simulation. For example, a parameter may be determined for a simulator that sets a minimum viable pH in the cytoplasm (below which the cell dies), and a variable may be identified that describes a current pH in the cytoplasm. The variable (current pH) might change throughout the simulation; however, the parameter (the minimum possible pH) would not change and remains fixed. An initial value of the pH variable may be identified, e.g., the value at the start of the simulation may be set in step 405 or if it is module specific then it may be set in step 420, and like the minimum pH parameter this would be used as an input into the simulation. The values of variables and parameters are both inputs, but the distinction is that variables can change from their initial values, and parameters are fixed throughout the simulation run.

At block 425, a time step is incremented, which can initially begin a given simulation. At block 430, for each module, module-specific input data is defined at least in part on the high-level data. More specifically, a high-level data structure may identify, for each of a set of molecules (e.g., metabolites), an availability value. Each availability value may initially be set to an initial availability value, which may thereafter be updated based on processing results from each module that relates to the molecule. For a given module, at each time step, a current availability value can be retrieved from the data structure for each molecule that pertains to the simulation technique assigned to the module. The module-specific input data may further include one or more lower-level values that are independent from processing of any other module. For example, one or more variables may only pertain to processing of a given module, such that the module-specific input data may further include an initial value or past output value that particularly and exclusively relates to the module.

At block 435, for each module, the configured simulator assigned to the module is run using the module-specific input data to generate one or more module-specific results. The one or more module-specific results may include (for example) one or more updated molecule availability values and/or a change in one or more availability values relative to corresponding values in the input data.

At block 440, results can be synthesized across modules. The synthesis may include summing differences across modules. For example, if a first module's results indicate that an availability of a given molecule is to be increased by 5 units and a second module's results indicate that an availability of the given metabolite is to be decreased by 3 units, a net change may be calculated as being an increase in 2 units. The net change can then be added to a corresponding availability value for the molecule that was used for the processing associated with the current time step and returned as a list of changes that should be made to the state vector. One or more limits may be applied to a change (e.g., to disallow changes across time steps that exceed a predefined threshold) and/or to a value (e.g., to disallow negative availability values and instead set the value to zero).

At block 445, the high-level data set is updated based on the synthesized results. The update can include adding data to a data structure such as a state vector from which one or more modules retrieve high-level data. The added data can include the synthesized results in association with an identifier of a current time step. Thus, the data structure can retain data indicating how an availability of a metabolite changed over time steps. It will be appreciated that alternatively the update can include replacing current high-level data with the synthesized data.

At block 450, it is determined whether the simulation is complete. The determination may be based on a number of time steps assessed, a degree to which data (e.g., high-level data) is changing across time steps, a determination as to whether a steady state has been reached, whether one or more simulated biological events (e.g., cell division or cell death) have been detected, etc. If the simulation is not complete, process 400 returns to block 425.

If the simulation is complete, process 400 continues to block 455, at which an output is generated. The output may include some or all of the high-level data and/or some or all of the module-specific results. For example, the output may include final availability values that correspond to a set of metabolites and/or a time course that indicates a change in the availability of each of one or more metabolites over the simulated time period. The output may be presented at a local device and/or transmitted to another device (e.g., for presentation).

Figure 5:
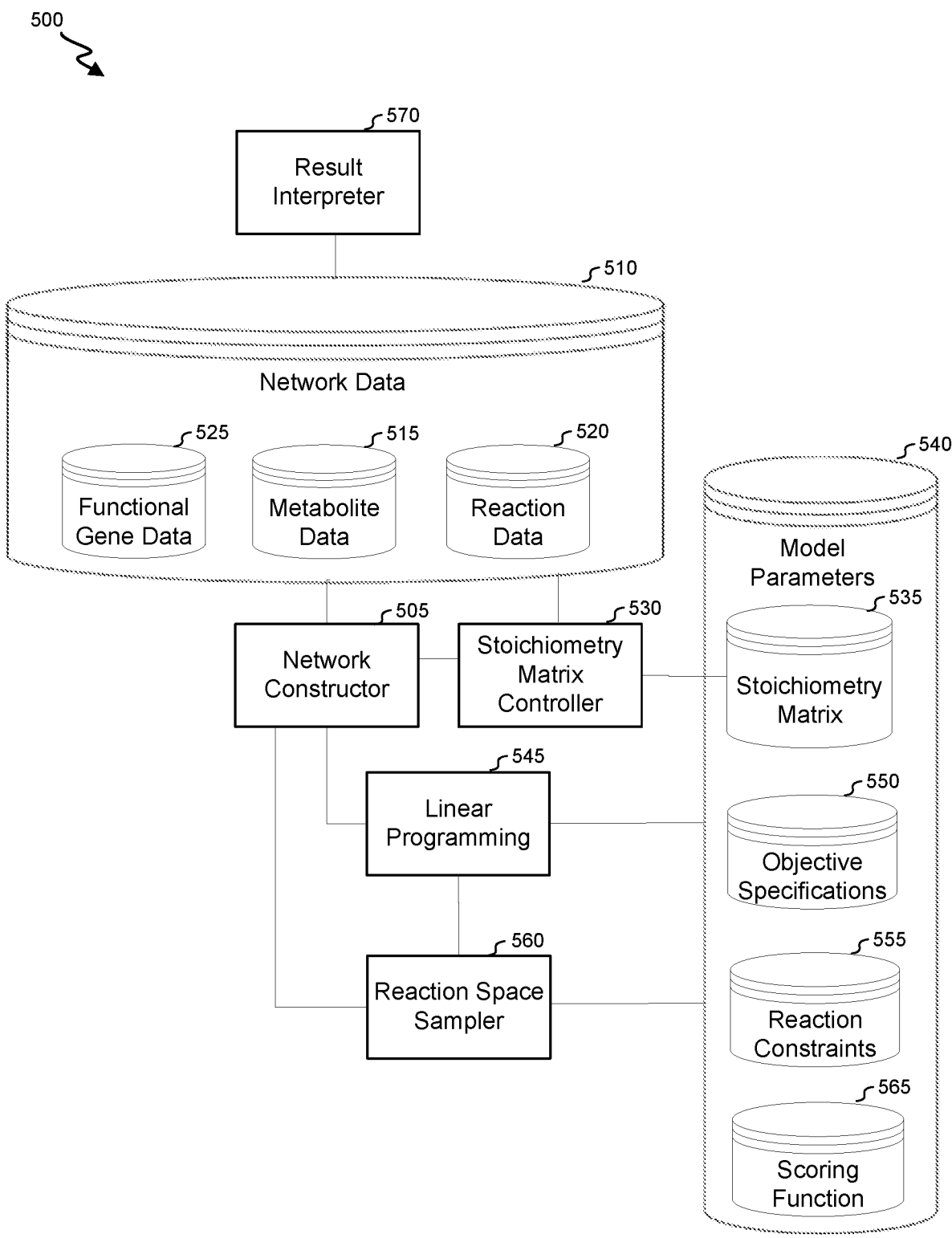
FIG. 5 shows a module-specific simulation controller to simulate states and reactions according to some embodiments of the invention.

FIG. 5 shows a module-specific simulation controller 200 to simulate states and reactions of modules configured by an integrated development environment (e.g., the interaction system 100 described with respect to FIG. 1) according to various embodiments. A network constructor 505 can be configured to use a model to simulate actions performed by a module of a biological system model (e.g., biological system model 200 as described with respect to FIG. 2). In some instances, the model is flux balance analysis, and/or the model is configured to solve for updated state values based on a set of equations that represent concentration changes in the network (e.g., a metabolic network). As should be understood to those of ordinary skill in the art, a biological system model such as a whole cell model does not have to include an FBA module. For example, from the framework described herein, biological processes such as core metabolism may be modeled that is completely different from FBA. In such an instance, part or all of the description and drawings pertaining to FIGS. 5 and 6 that is specific to FBA (e.g., objective functions, constraints, and linear programming) may not be relevant to that particular instantiation of the model or to simulations run with that model. However, many of the components and techniques described with respect to FIGS. 5 and 6 could be applied to simulate states and reactions of modules implemented by other models. For example, any module can read values from the state vector and return an indication of one or more changes that should be made to the state vector. The FBA module (if it's even present in a particular instantiation of the model) may read and return more values than any other model, but a module modeled with FBA need not be handled by the simulation controller 300 any differently from other modules and/or models described herein.

Network constructor 505 can access a set of network data (e.g., parameters and variables) stored in a network data store 510 to define the model. Metabolite data 515 can identify each metabolite of a metabolome. As used herein, a "metabolite" is any substance that is a product of metabolic action or that is involved in a metabolic process including (for example) each compound input into a metabolic reaction, each compound produced by a metabolic reaction, each enzyme associated with a metabolic reaction, and each cofactor associated with a metabolic reaction. The metabolite data 515 may include for each metabolite (for example) one or more of the following: the name of the metabolite, a description, neutral formula, charged formula, charge, spatial compartment of the biological system and/or module of the model, and identifier such as PubChem ID. Further, metabolite data 515 can identify an initial state value (e.g., an initial concentration and/or number of discrete instances) for each metabolite.

Reaction data 520 can identify each reaction (e.g., each metabolic reaction) associated with the model. For example, a reaction can indicate that one or more first metabolites is transformed into one or more second metabolites. The reaction need not identify one-to-one relationships. For example, multiple metabolites may be defined as reaction inputs and/or multiple metabolites may be defined as reaction outputs. The reaction data 520 may include for each reaction (for example) one or more of the following: the name of the reaction, a reaction description, the reaction formula, a gene-reaction association, genes, proteins, spatial compartment of the biological system and/or module of the model, and reaction direction. Further, the reaction data 520 can identify, for each metabolite of the reaction, a quantity of the metabolite, which may reflect the relative input-output quantities of the involved metabolites. For example, a reaction may indicate that two first metabolites and one second metabolite are input into a reaction and that two third metabolites are outputs of the reaction. The reaction data 520 can further identify an enzyme and/or cofactor that is required for the reaction to occur.

Functional gene data 525 can identify genes and relationships between genes, proteins, and reactions, which combined provide a biochemically, genetically, and genomically structured knowledge base or matrix. Functional gene data 525 may include (for example) one or more of the following: chromosome sequence data, the location, length, direction and essentiality of each gene, genomic sequence data, the organization and promoter of transcription units, expression and degradation rate of each RNA transcript, the specific folding and maturation pathway of RNA and protein species, the subunit composition of each macromolecular complex, and the binding sites and footprint of DNA-binding proteins. Network constructor 505 can use functional gene data and the availability of proteins encoded by those genes to update reaction constraints. One exemplary technique by which genomic data can be associated with reaction data is evaluating Gene-Protein-Reaction expressions (GPR), which associate reactions with specific genes that triggered the formation of one or more specific proteins. Typically a GPR takes the form (Gene A AND Gene B) to indicate that the products of genes A and B are protein subunits that assemble to form a complete protein and therefore the absence of either would result in deletion of the reaction. On the other hand, if the GPR is (Gene A OR Gene B) it implies that the products of genes A and B are isozymes (i.e., each of two or more enzymes with identical function but different structure) and therefore absence of one may not result in deletion of the reaction. Therefore, it is possible to evaluate the effect of single or multiple gene deletions by evaluation of the GPR as a Boolean expression. If the GPR evaluates to false, the reaction is constrained to zero in the model.

A stoichiometry matrix controller 530 can use reaction data 520 to generate a stoichiometry matrix 535. Along a first dimension of the matrix, different compounds (e.g., different metabolites) are represented. Along a second dimension of the matrix, different reactions are represented. Thus, a given cell within the matrix relates to a particular compound and a particular reaction. A value of that cell is set to 0 if the compound is not involved in the reaction, a postive value if the compound is one produced by the reaction and a negative value if the compound is one consumed by the reaction. The value itself corresponds to a cofficient of the reaction indicating a quantity of the compound that is produced or consumed relative to other compound consumption or production involved in the reaction.

Because frequently relatively few reactions correspond to a given compound, stoichiometry matrix 535 can be a sparse stoichiometry matrix. Stoichiometry matrix 505 can be part of a set of model parameters (stored in a model-parameter data store 540) used to execute a module.

One or more modules may be configured to use linear programming 545 to identify a set of compound quantities that correspond to balancing fluxes identified in reactions represented in stoichiometry matrix 535. Specifically, an equation can be defined whereby the product of stoichiometry matrix 535 and a vector representing a quantity for each of some of the compound quantities is set to zero. (It will be appreciated that the reactions may further include quantities for one or more boundary metabolites, for which production and consumption need not be balanced.) There are frequently multiple solutions to this problem. Therefore, an objective function is defined, and a particular solution that corresponds to a maximum or minimum objective function is selected as the solution. The objective function can be defined as the product between a transposed vector of objective weights and a vector representing the quantity for each compound. Notably, the transposed vector may have a length that is equal to the first dimension of stoichiometry matrix 535, given that multiple reactions may relate to a same compound.

The objective weights may be determined based on objective specifications 550, which may (for example) identify one or more reaction-produced compounds that are to be maximized. For example, the objective weights can be of particular proportions of compounds that correspond to biomass, such that producing compounds having those proportions corresponds to supporting growth of the biological system.

Each reaction may (but need not) be associated with one or more of a set of reaction constraints 555. A reaction constraint may (for example) constrain a flux through the reaction and/or enforce limits on the quantity of one or more compounds consumed by the reaction and/or one or more compounds produced by the reaction.

In some instances, linear programming 545 uses stoichiometry matrix 535 and reaction constraints 550 to identify multiple solutions, each complying with the constraints. When multiple solutions are identified, objective specifications 550 can be used to select from amongst the potential solutions. However, in some instances, no solution is identified that complies with stoichiometry matrix 535 and reaction constraints 555 and/or the only solution that complies with the matrix and constraints is not to proceed with any reaction.

A solution can include one in which, for each of a set of metabolites, a consumption of the metabolite is equal to a production of the metabolite. That is not to say that this balance must be achieved for each metabolite, as a set of reactions involve one or more "boundary metabolites" for which this balance is not achieved. For example, glucose can be consumed at a given rate, and/or acetate can be produced at a given rate.

Reaction data 520 may further identify an objective function that identifies a target product (e.g., representing cell growth rate) that is to be maximized. The objective function can identify particular ratios of multiple reactant metabolites that must be available to produce the product. Strictly enforcing the objective function may result in simulating no growth if a single metabolite is not produced. An alternative approach is to define one or more objective functions configured such that production of each of multiple target reactant metabolites that relate to the target product is to be maximized. A higher level whole-cell model can evaluate the production of multiple target reactant metabolites to determine whether to and/or an extent to which to simulate growth. For example, depending on which target reactant metabolite(s) are not produced, the whole-cell model may nonetheless simulate cell growth, simulate cell growth at a reduced rate, simulate no growth, simulate unhealthy or impaired growth or simulate cell death.

For example, a reaction space can be defined based on stoichiometry matrix 535 and reaction constraints 555. The space may have as many dimensions as there are reactions. Each dimension can be restricted to include only integer values that extend along a range constrained by any applicable constraint in reaction constraints 555. A reaction space sampler 560 can then determine, for each of some or all of the points within the reaction space, a cumulative quantity of each metabolite that would be produced based on the associated reactions. Reaction space sampler 560 can compare these quantities to those in the objective vector (e.g., by determining an extent to which proportions of compounds are consistent).

In these instances, a scoring function 565 can indicate how to score each comparison. For example if proportions of each of two potential solutions differ from the objective proportions by 2, but one potential solution differs by 2 for a single compound and another by 1 for each of two compounds, scoring function 565 can be configured to differentially score these instances. For example, different weights may be applied to different compounds, such that differences that affect a first compound are more heavily penalized than differences that affect a second compound. As another example, scoring function 565 may indicate whether a score is to be calculated by (for example) summing all compound-specific (e.g., weighted) differences, summing an absolute value of all compound-specific (e.g., weighted) differences, summing a square of all compound-specific (e.g., weighted) differences, etc. Reaction space sampler 560 can then identify a solution as corresponding to reaction coefficients that are associated with a highest score across the reaction space.

Network constructor 505 can receive results from each of linear programming 545 and/or reaction space sample 560. In some instances, linear programming 545 can further avail its results to reaction space sample 560. When a balanced solution is identified by linear programming 545, reaction space sampler 560 need not sample the reaction space and need not avail reaction-space results to network constructor 505.

Network constructor 505 can identify a solution as corresponding to one identified by linear programming 545 when a balanced solution is identified and as a highest-score potential solution identified by reaction space sampler 560 otherwise. The solution can then indicate the compounds produced by and consumed by the reactions performed in accordance with the solution-indicated flux. Network constructor 505 can update metabolite data 515 based on this production and consumption.

In some instances, a solution is identified for each of a set of time points rather than only identifying one final solution. The iterative time-based approach may be useful when module-specific simulation controller 500 is but one of a set of simulation controllers and metabolite data 515 is influenced by the performance of other modules. For example, metabolite data 515 may be shared across modules or may be defined to be a copy of at least part of a cross-module metabolite data set at each time point. The updates to the metabolites performed by network constructor 505 may then be one of multiple updates. For example, an update by network constructor 505 may indicate that a quantity of a specific metabolite is to increase by four, while a result from another module indicates that a quantity of the specific metabolite is to decrease by two. Then the metabolite may change by a net of +2 for the next time iteration.

A results interpreter 570 can generate one or more results based on the updated metabolite data 515. For example, a result may characterize a degree of growth between an initial state and a steady state or final time point. The degree of growth may be determined based on a ratio between values of one or more metabolites at a current or final time point relative to corresponding values at an initial (or previous) time point. The one or more metabolites may correspond to (for example) those identified in an objective function as corresponding to biomass growth. As another example, a result may characterize a time course of growth. For example, a result may identify a time required for metabolite changes that correspond to a representation of a double in growth or a time constant determined based on a fit to values of one or more time series of metabolite values. The result(s) may be output (e.g., locally presented or transmitted to a remote device, such as a user device). The output can facilitate a presentation of an interface that indicates one or more simulation characteristics (e.g., one or more default values in terms of initial-state values or reaction data and/or one or more effected perturbations).

Operation of module-specific simulation controller 500 can be influenced by particular simulated perturbations of the whole cell. For example, each perturbation may correspond to a particular type of genetic mutation. The perturbation may have been identified based on detecting user input (e.g., a selection and/or text input received via an interface) that defines the perturbation. One exemplary type of perturbation is a gene mutation. An effect of the perturbation may be determined based on functional gene data (e.g., to determine how an availability of one or more metabolites is affected). High-level metabolite data, simulator parameters and/or high-level constraints may then be accordingly set, constrained and/or defined based on the perturbation. This high-level perturbation can thus then influence operation of one or more lower level modules.

Figure 6:
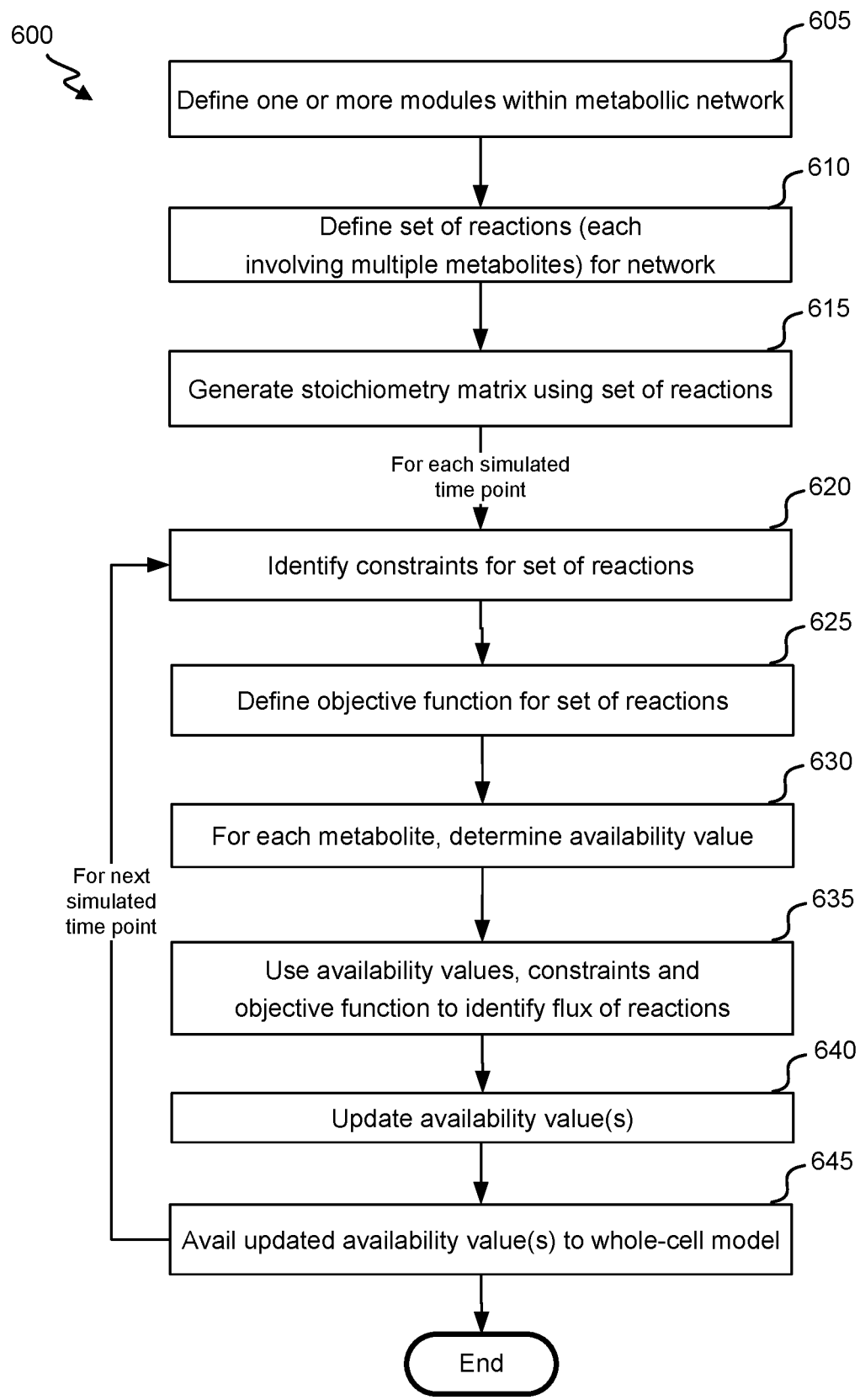
FIG. 6 shows a process for using a simulator to generate metabolite time-course data according to an embodiment of the invention.

FIG. 6 shows a process 600 for using a simulator to generate metabolite time-course data according to various embodiments. In some embodiments, the processes depicted in process 600 are implemented by the interaction system 100 of FIG. 1, and discussed with respect to the module-specific simulation controller 500 of FIG. 5. Process 600 begins at block 605, at which a one or more modules within a metabolic network (e.g., of a biological system) are defined. The module(s) can be defined based on which parts of the network exhibit relative functional independence and/or correspond to substantial independence in terms of biological activity. In some instances, a default is to define each part of a cell as part of a core module unless a different module corresponding to particular types of actions and/or cell components is defined.

At block 610, a set of reactions is defined for the network. In some instances, the set of reactions are defined for the module (or each module) that corresponds to the default model type. The set of reactions can indicate how various molecules such as metabolites are consumed and produced through part of all of a life cycle of a biological system. Each reaction thus identifies one or more metabolites that are consumed, one or more metabolites that are produced and, for each consumed and produced metabolite, a coefficient (which may be set to equal one) indicating a relative amount that is consumed or produced. The reaction may further include an identification of one or more enzymes, one or my cofactors and/or one or more environmental characteristics that are required for the reaction to occur and/or that otherwise affects a probability of the reaction occurring or a property of the reaction. The reactions may be identified based on (for example) online or local digital content (e.g., from one or more scientific papers or databases) and/or results from one or more wet-lab experiments.

At block 615, a stoichiometry matrix is generated using the set of reactions. Each matrix cell within the matrix can correspond to a particular metabolite and a particular reaction. The value of the cell may reflect a coefficient of the particular metabolite within the particular reaction (as indicated in the reaction) and may be set to zero if it is not involved in the reaction. In some instances, metadata is further generated that indicates, for each of one or more reactions, any enzyme, co-factor and/or environmental condition required for the reaction to occur.

At block 620, one or more constraints are identified for the set of reactions. In some instances, identifying the constraints may include identifying values for one or more parameters. For example, for each of one or more or all of the set of reactions, a constraint may include a flux lower bound and/or a flux upper bound to limit a flux, a quantity of a consumed or produced metabolite, a kinetic constant, a rate of production or decay of a component such as RNA transcript, an enzyme concentration or activity, a compartment size, and/or a concentration of an external metabolite.

The constraint(s) may be identified based on (for example) user input, online or local data, one or more communications from a wet-lab system, and/or learned from statistical inference.

At block 625, an objective function is defined for the set of reactions. The objective function may identify what is to be maximized and/or what is to be minimized while identifying a solution. The objective function may (for example) identify a metabolite that is produced by one or more reactions or a combination of metabolites that is produced by one or more reactions. The combination may identify proportions of the metabolites. However, the objective function can have a number of limitations and may fail to reflect supply and demand within the other modules. Thus, in some instances, a limited objective function can be constructed to include a set of target values for each molecule within the metabolic network. The target values can incorporate intrinsic-rate parameters, supply rates of molecules, the consumption rates of molecules, and the molecule concentrations into a measurement of target concentrations of the molecule given supply, demand, and an "on-hand" concentration of each molecule, which represents the concentration of a molecule immediately available to a reaction pathway. The target values may be calculated and incorporated into the objective function to produce the limited objective function. This may be in the form of calculating an absolute difference between the target value and the proportional flux contribution of each molecule. This may be in the form of scaling the proportional flux contribution of each molecule. This may be in the form of adding to the proportional flux contribution of each molecule. Any other mathematical modification of the proportional flux contribution of each molecule that adjusts this value by the target value may be used. The target values may be positive or negative. For purposes of unit conversion, so that target values can be included in the objective function and compared to the flux values, the target values may be constructed as rates.

At block 530, for each metabolite related to the set of reactions, an availability value is determined. For an initial value, the value may be identified based on (for example) user input, digital content and/or communication from another system. Subsequent values may be retrieved from a local or remote data object that maintains centralized availability values for the set of metabolites.

At block 635, the availability values, constraints and objective function are used to determine the flux of one, more or all of the set of reactions. The flux(es) may indicate a number of times that each of one, more or all of the reactions were performed in a simulation in accordance with the availability values, constraints and objective function. The flux(es) may be determined based on a flux-balance-analysis model. In some instances, the flux(es) may be determined based on a sampling of all or part of an input space representing different flux combinations and scoring each input-space using a scoring function.

At block 640, a centralized availability value of one or more metabolites is updated based on the determined flux(es). More specifically, for each metabolite, a cumulative change in the metabolite's availability may be identified based on the cumulative consumption and cumulative production of the metabolite across the flux-adjusted set of reactions. The centralized availability value of the metabolite can then be incremented and/or decremented accordingly.

In some instances, at least one the one or more modules defined at block 605 are to be associated with a model that does not depend on (for example) a stoichiometry matrix and/or flux based analysis and/or that is based on physiological modeling. One or more modules based on one or more different types of models can also, at each time point, identify a change in metabolite availability values, and such changes can also be used to update a local or remote data object with centralized availability values. With respect to each metabolite, updates in availability values may be summed to identify a total change and/or updated availability value. In some instances, limits are set with respect to a maximum change that may be effected across subsequent time steps and/or a maximum or minimum availability value for a metabolite.

At block 645, availability data is availed to a higher-level model. State vectors can then be updated based on data from multiple modules.

Some or all of blocks 620-645 may be repeated for each of multiple simulated time points in a simulation. Thus, at each time point, constraints can be updated based on state-vector information (e.g., representing availability of catalysts), an objective function can be defined (e.g., which may change across time points based on a configuration of a higher level objective), updated metabolite availability values can be determined, updated reaction fluxes can be identified, and further updated availability values can be determined. In some instances, a predefined number of simulated time points are to be evaluated and/or simulated time points corresponding to a predefined cumulative time-elapsing period are to be evaluated. In some instances, a subsequent simulated time point is to be evaluated until a predefined condition is satisfied. For example, a predefined condition may indicate that metabolite values for a current simulated time point are the same or substantially similar as compared to a preceding simulated time point or a preceding simulated time period.

With regard to a repeated iteration of block 630, it will be appreciated that an availability value determined for a given metabolite need not be equal to the corresponding updated availability value from the previous iteration of block 640 and/or the sum of the previously determined availability value adjusted by the identified flux pertaining to the metabolite. Rather, a processing of the previous time point with respect one or more other modules may have also resulted in a change in the metabolite availability, and/or a higher level constraint and/or processing may influence the availability. Thus, the availability value for a given metabolite determined at block 630 for a current time point may be equal to the availability value determined at block 630 for a preceding time point plus the cumulative updates to the availability value across modules, with any limits imposed.

While not shown in process 600, one or more variables can be output (e.g., transmitted to a user device). The variable(s) may include final values (e.g., availability values after all iterations have been performed), time-course values, high-level values and/or module-specific values. For example, the availability data may include, for each of one, more or all metabolites: an availability value (e.g., a final availability value) and/or a time course of the availability value. In some instances, the availability data is output with reference availability data. For example, when part or all of the processing performed to calculate the availability values was associated with a perturbation, the reference availability data may be associated with an unperturbed state. In some instances, a processed version of the availability data is output. For example, a comparison of availability values for particular metabolites across time points may be used to generate one or more growth metrics (e.g., a growth magnitude or rate), which may be output. Outputting the availability data can include (for example) locally presenting the availability data and/or transmitting the availability data to another device.

Figure 7:
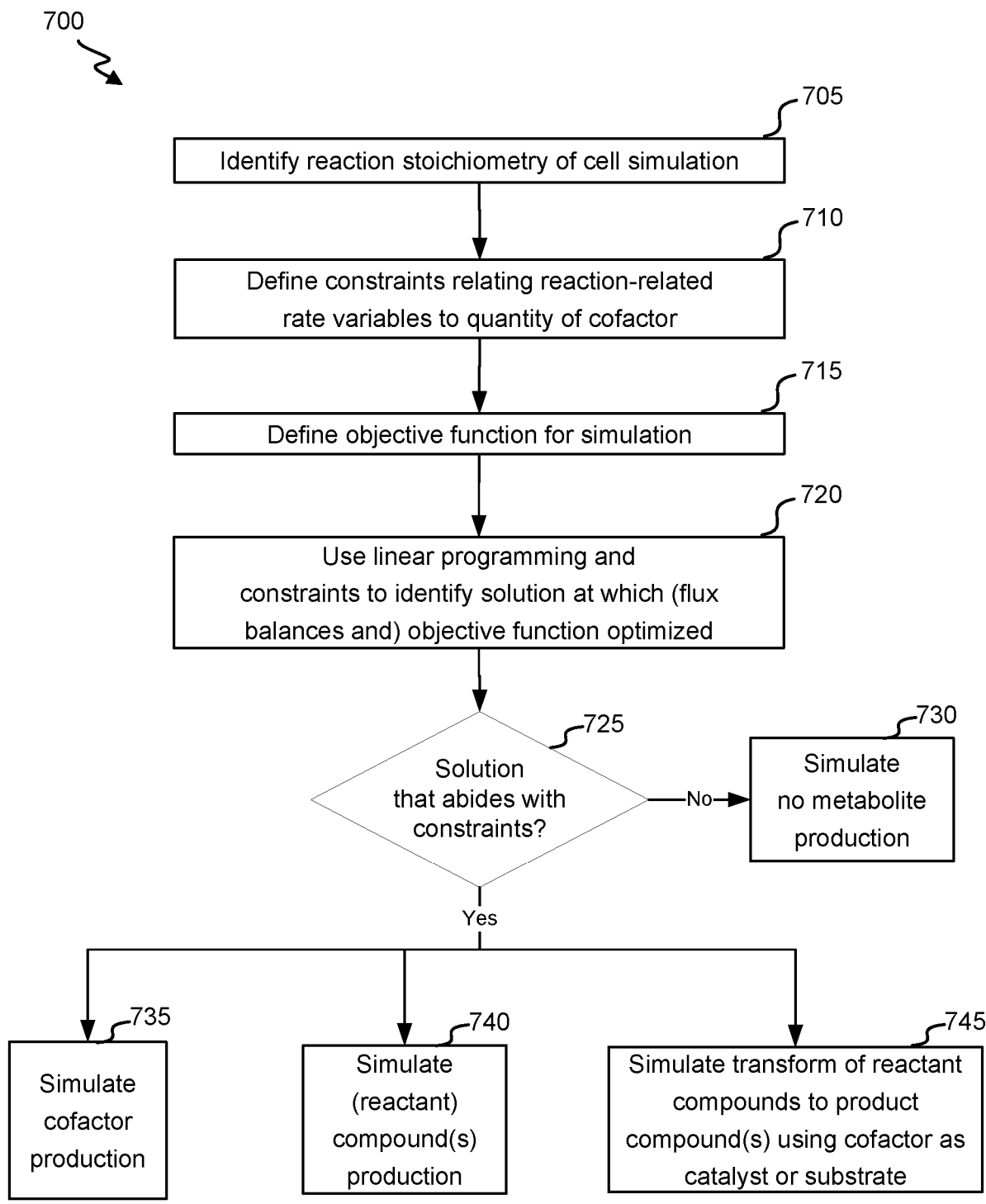
FIG. 7 shows a process for simulating network activity according to an embodiment of the invention.

FIG. 7 shows a process 700 for simulating network activity according to an embodiment of the invention. In some instances, process 700 can be a variation of process 600. Process 700 begins at block 705, at which reaction stoichiometry of a cell simulation is identified. The reaction stoichiometry can pertain to a simulation of an entire cell or to a module of the cell. The reaction stoichiometry can represent a set of reactions. For example, a first reaction can simulate dephosphorylation of a compound (e.g., undecaprenyl) and one or more second reactions can simulate returning the compound to a phosphorylated state. Each reaction in the set of reactions can identify a set of metabolites. More specifically, each reaction in the set of reactions can identify one or more reactant compounds (e.g., a ligand and/or a substrate) that are consumed during the reaction and one or more product compounds that are produced during the reaction.

Further, a reaction may (but need not) include one or more non-consumed compounds, which may function as a catalyst for the reaction. For example, a non-consumed compound may include an enzyme, cofactor or ribosome. Exemplary specific non-consumed compounds include: folate, undecaprenyl, nicotinamide adenine dinucleotide (NAD), nicotinamide adenine dinucleotide phosphate (NADP), Flavin adenine dinucleotide (FAD), menaquinone, and coenzyme A (CoA). Because the non-consumed compound is not consumed, it can be reused across different reactions. In some instances, a subset of the set of reactions identify a cycle that recycles a non-consumed compound.

Stoichiometry can identify relative quantities between each compound in a given reaction. In some instances, the reaction stoichiometry is reduced to lowest common whole ratios (such that a lowest coefficient in a reaction's stoichiometry representation is one). In some instances, involvement of a non-consumed compound in a reaction or series of reactions is not represented in the reaction or series of reactions themselves. Rather, metadata associated with the reaction or series of reactions may identify the role of the non-consumed compound.

At block 710, one or more constraints for the simulation are defined. In some instances, the reaction stoichiometry can itself serve as constraints on simulation solutions, though additional constraints can further be applied. The additional constraints may correspond to (for example) simulated environmental conditions and/or empirical bounds (e.g., on metabolite levels, reaction prominence, and/or changes in metabolite or reaction levels). Thus, a constraint may be configured to restrict a flux value identified for each of one, more or all reaction. In some instances, the additional constraints are identified based on user input.

In some instances, a constraint is configured to restrict a flux value of one or more reactions (or series of reactions) based on a quantity or count of a metabolite. The metabolite can include a non-consumed compound, such as a cofactor, enzyme or ribosome. Given that the compound is not consumed by a given reaction or across a series of reactions (e.g., when it starts and ends the series as the same compound), the compound may be repeatedly used. However, a rate at which it can be repeatedly used and thus a rate at which it can facilitate producing a product compound can be limited based on a duration of time during which it is involved in the reaction or series of reactions (e.g., a sequestration duration). The duration may be identified based on (for example) user input, using a look-up table, from experimental data, etc. Thus, a flux for a given reaction or series of reactions (indicating a number of reactions or series of reactions using the non-consumed compound that may be performed during a period of time) may be capped at a quantity of the non-consumed compound indicated as being present in the simulation divided by a sequestration time of the non-consumed compound in the given reaction or series of reactions.

In some instances, a set of reactions or metadata indicate that the non-consumed compound is involved in and/or is required for multiple reactions (e.g., such that the non-consumed compound is available in its initial state upon completion of each of the multiple reactions) or multiple series of reactions (e.g., such that each of the non-consumed compound is available in its initial state upon completion of each of the series of reactions) or a combination of at least one reaction and at least one series of reactions. When the non-consumed compound is involved in and/or required in a series of reactions, the non-consumed compound may (but need not) be partly transformed through part of the series and then return to its initial state (e.g., first becoming dephosphorylated and then phosphorylated or first binding to another compound and then becoming unbound).

In these instances, each of the reactions or series of reactions may be associated with a different sequestration duration and/or a different flux value. Thus, the constraint may be defined based on one or more characteristics of the reuse of the non-consumed compound across cycles of each of the associated reactions or reaction series. The one or more characteristics can include a duration (e.g., sequestration duration) and/or a flux value of each of the associated reactions or reaction series. For example, an intermediate value may be generated for each reaction or reaction series (that results in a to-be-reused non-consumed compound) that is set to equal a product of a sequestration duration and flux of the reaction or reaction series. The constraint can indicate that a quantity (e.g., number or concentration derived therefrom) of the non-consumed compound is to be set to be at least equal to a sum of the intermediate values. This sum can be representative of - at maximum efficiency of use of non-consumed compound - a quantity of the non-consumed compounds that are being "used" by the simulated reactions. Thus, a quantity of the non-consumed compound must be at least equal to this sum. The duration (e.g., sequestration duration) may identify a per-cycle (or per-iteration) time during which the non-consumed compound is involved with the reaction or reaction series.

At block 715, an objective function for the simulation is defined. The objective function may identify one or more metrics that are to be maximized and/or minimized when identifying a solution. In some instances, a metric corresponds to a set of values. For example, defining an objective function so as to indicate that biomass growth is to be maximized can include identifying a particular set of compounds and relative quantities thereof that are representative of biomass levels.

At block 720, a solution is identified using linear programming (e.g., using linear algebra) and the constraints. The solution may be one that abides by each defined constraint. In some instances, many potential solutions abide by all constraints, and thus, the objective function can be used to identify a single solution to select for the simulation (e.g., one that maximizes a given objective, minimizes a given objective or corresponds to a highest/lowest statistic based on objective evaluations).

In some instances, the solution is one for which fluxes are balanced, in that quantities of compounds that are produced by the set of reactions are equal to quantities of compounds that are consumed by the set of reactions. When the set of reactions correspond to a model of an entire network, this corresponds to a steady-state solution. When the set of reactions corresponds to a module of a network and when values are synthesized across modules between time steps, the solution need not correspond to a steady-state solution. In some instances, flux balancing is an objective instead of a constraint, such that balancing fluxes to the extent possible is one of one or more factors used to identify a given solution across one or more possible solutions but is not a requirement for identifying a solution.

At block 725, it is determined whether a solution that abides with the constraint(s) has been identified. If not, process 700 proceeds to block 730, at which a result indicates that metabolites are not produced in the simulation. A whole-cell model may receive an indication of a lack of metabolite production associated with the module and determine how the cell simulation is to be affected (e.g., nonetheless grow, impaired or inhibited growth, no growth or cell death).

When the linear programming did produce a solution, process 700 proceeds to blocks 735, 740 and 745 (which may be performed concurrently and/or in parallel). At block 735, cofactor production is simulated in accordance with the solution. Depending on the particular solution, block 735 need not occur. For example, the cofactors used in the reactions may entirely correspond to recycled cofactors (e.g., that were produced at previous time steps and//or recycled from previous cycle iterations).

At block 740, production of one or more compounds is simulated in accordance with the solution. Each of the one or more compounds can be produced in accordance with at least one of the set of reactions. Each of at least one of the one or more compounds that are produced may function as a ligand or substrate of another reaction. Though physiologically a given compound may first need to be produced before it can be consumed by a subsequent reaction, the simulation may simulate these reactions concurrently or even in reverse order in response to identifying a solution that indicates that both reactions are to occur.

At block 745, one or more reactions that use the cofactor are simulated. The one or more reactions can be configured to transform the one or more compounds to one or more product compounds. The one or more compounds that are transformed can include compounds that are produced at block 740. The cofactor is not consumed during the transformation, in that it is availed for reuse during a subsequent reaction-based transformation after the product compound(s) are produced for a given iteration.

The potential concurrent or parallel operation of blocks 735-745 and linear-programming solution identifications indicate how a simulation may identify a solution that would require more cofactors to support the solution-identified reactions than actually present in the simulation. Specifically, the concurrent or parallel processing can fail to account for order requirements physiologically necessary for reaction performance. That is, if reactions indicate that a production and consumption of a given compound would be equal, the compound can be deemed to be balanced. That is, an initial consumption reaction may essentially "borrow" the compound from a subsequent production reaction. Thus, even if the compound is never initially produced, flux-balance analysis may allow simulated reactions that use the compound to occur if the reactions indicate that an amount of the compound that is used is less than or equal to an amount of the compound that is subsequently produced.

It will be appreciated that variations of process 700 are contemplated. For example, rather than defining a constraint that relates a quantity of a non-consumed compound to sequestration durations and fluxes, this relationship may be integrated into an objective function. For example, an objective may be defined that indicates that a quantity of a non-consumed compound is to be at least equal to a product of sequestration duration and a flux of a reaction or series thereof (or a sum of these products across multiple reactions, multiple reaction series or a combination of multiple reactions and one or more reactions series if each reaction and/or series involves the non-consumed compound).

Further, while process 700 corresponds to constraints that pertain to a cofactor, another type of non-consumed compound can be alternatively or additionally constrained. For example, a constraint may relate to an enzyme or ribosome.

Figure 8:
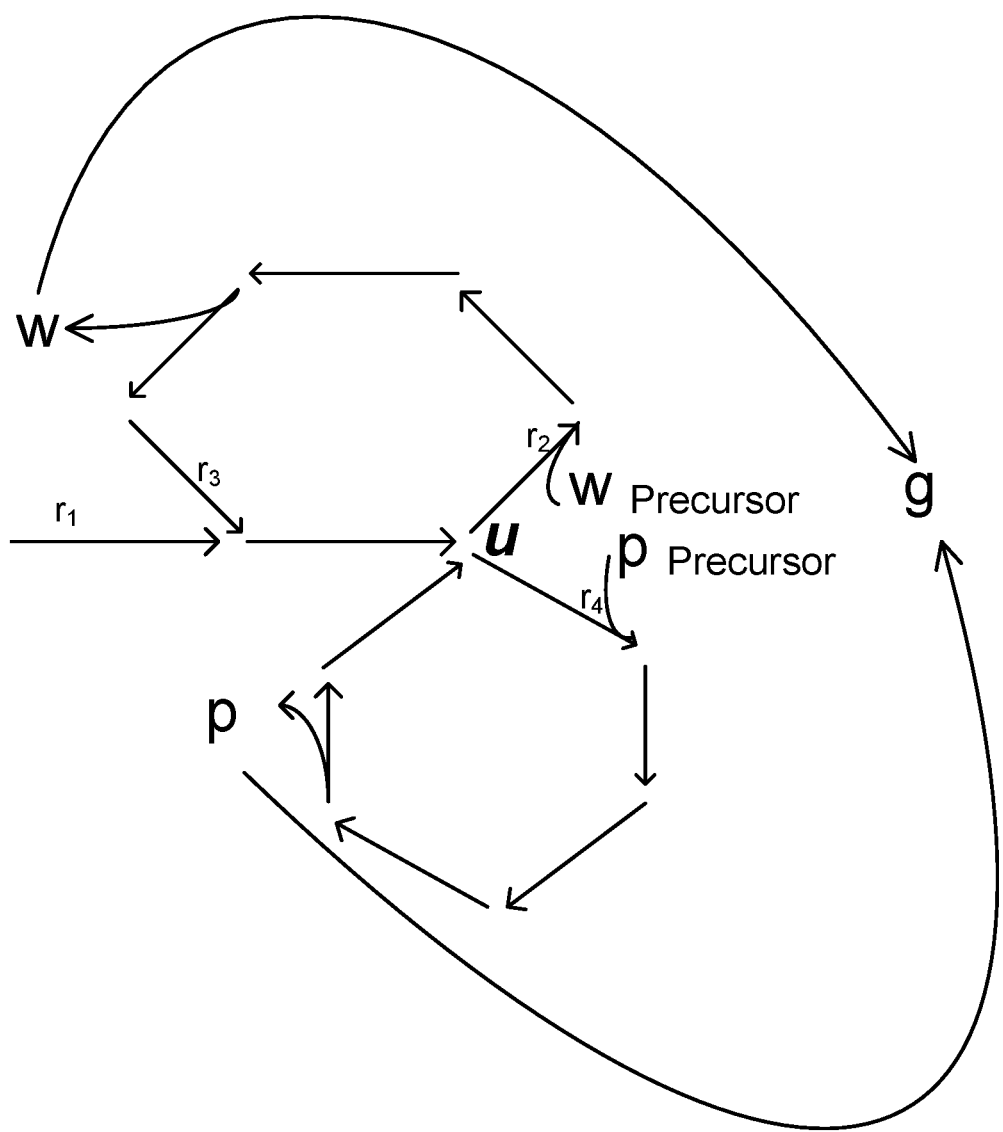
FIG. 8 shows a representation of reaction series in which a non-consumed component is used.

FIG. 8 shows a representation of reaction series in which a non-consumed component is used. In this example, the non-consumed component is a cofactor undecaprenyl (depicted as "u"). It is used in two series of reactions: one to produce peptidoglycan (depicted as "p") and one to produce the wall teichoic acid (WTA, depicted as "w"). Each of peptidoglycan and WTA is a structural component of the cell wall of Staphylococcus aureus and required for growth. In each of the reactions, undecaprenyl is recycled, such that it can be used in a subsequent reaction series.

Though undecaprenyl is required for the production of each of peptidoglycan and WTA, it can only support one reaction series at a time. Thus, if a given undecaprenyl compound is supporting a reaction series for producing peptidoglycan, in the simulation, it cannot concurrently support a reaction series for producing WTA. Further, while FIG. 8 depicts only a single (alternative) pair of series of reactions, multiple iterations of each of the pair may be concurrently occurring.

Physiologically, a total quantity of the undecaprenyl compounds that is used in the simulation across both reaction series cannot exceed a sum of those produced and those recycled across previous iterations of the cycle. Further, the quantity of WTA that is produced cannot exceed the quantity of precursors of WTA that is consumed in the reaction or the quantity of undecaprenyl that is available. Similarly, the quantity of peptidoylcan that is produced cannot exceed the quantity of precursors of peptidoyclan that is consumed in the reaction or the quantity of undecaprenyl that is available.

Figure 9:
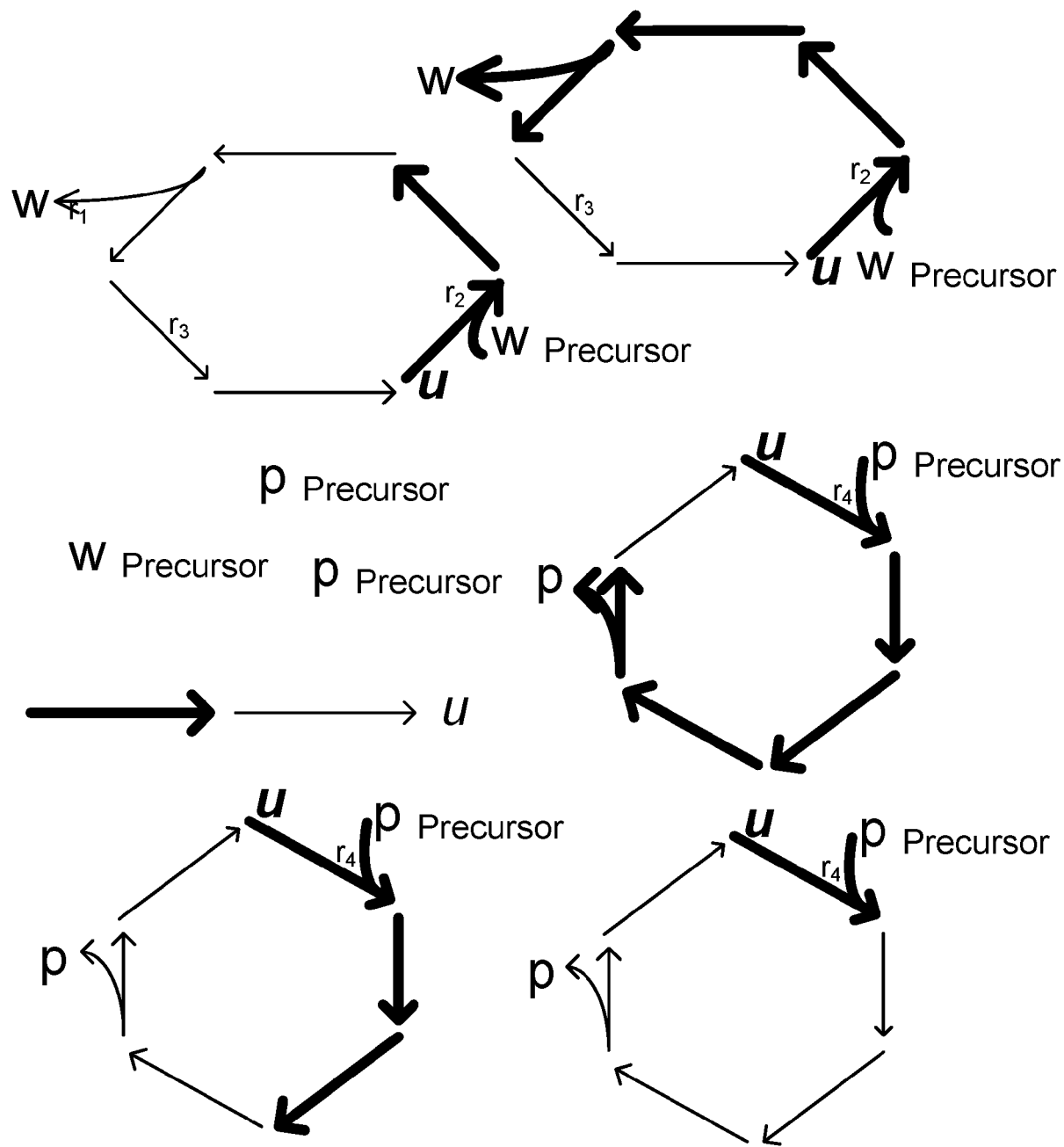
FIG. 9 shows a partial representation of physiological states of a reaction according to an embodiment of the invention.

FIG. 9 shows a partial representation of physiological states of a reaction according to an embodiment of the invention. The representation illustrates that, physiologically, at any point in time, a reaction cycle may be occurring in multiple instances. A degree through which an instance has progressed through the cycle can vary (at the point in time) across instances. For example, FIG. 9 includes an illustration in which each of the reaction series include six discrete reactions. At a given temporal snapshot (represented by the figure), a state of the reaction series is represented by the bolded line, in that the representation indicates that a given instance has performed or is performing each of the reactions represented along the bolded line. As illustrated, the state of the reaction series differs across the instances. Specifically, each reaction series is at a different reaction within the series. (While the depicted illustration represents each instance as corresponding to a different reaction state, it will appreciated that multiple instances may correspond to a given state.)

In each series, undecaprenyl is not released and availed for a different reaction until the series is complete. Thus, none of the five undecaprenyls associated with the five reaction series can, at the represented time, support transforming the available precursors of peptidoyclan or WTA (as represented by the floating pprecursor and WPrecursor representations). FIG. 9 also shows a representation of a reaction series to synthesize undecaprenyl. However, as indicated by the bolded elements, this synthesis is not yet complete, such that it has yet to produce an undecaprenyl that can be used interact with a peptidoyclan precursor or WTA precursor.

This representation illustrates how a flux of one or more reactions can be constrained by a quantity of a non-consumed compound and how the relationship between the flux and quantity further depends on a speed of a reaction series. For example, if each of the reaction series was performed very quickly, a single non-consumed compound could support many reaction series within a time period despite being unable to concurrently support multiple series.

As noted herein, integrating a core module into a whole-cell model facilitates tracking a quantity of non-consumed compounds (based on prior production of the compound). Further the integration can facilitate tracking availability of non-consumed compounds (based on time cycles of reactions within a reaction series relative to time steps). Thus, reactions are not supported by a fictitious limitless supply of non-consumed compounds. For example, in the depicted instance, even if multiple peptidoyclan precursors were available, if a state vector indicated that all undecaprenyl were involved in a current reaction series, a simulation may refrain from initiating another peptidoyclan cycle. If at a next time step, two undecaprenyls were available (one as a result of a completion of a reaction series and another as a result of a new production), two new simulated reaction series could be initiated.

Figure 10:
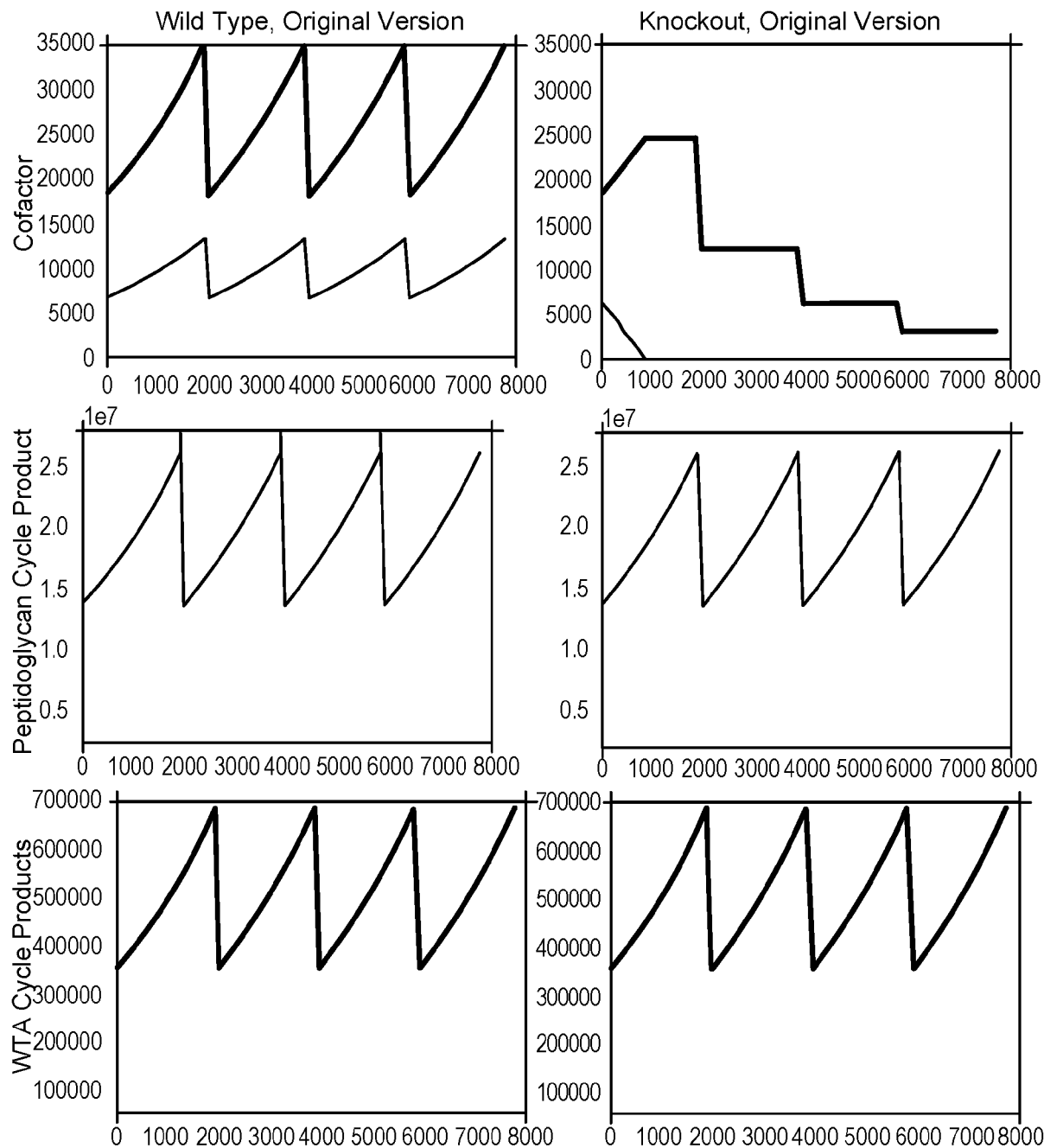
FIG. 10 shows examples of dynamics of components of a simulated network.

FIG. 10 shows examples of dynamics of components of a simulated network. A flux-balance module of the network can be configured to determine, for each of a set of reactions, a flux that indicates a frequency at which the reaction is performed. The set of reactions can represent core metabolism, membrane synthesis and cell wall synthesis. The fluxes can be determined by identifying a solution space that includes a set of potential solutions that meet each of a set of predefined constraints. Each potential solution can identify a flux value for each of the set of reactions. In this instance, the set of predefined constraints does not include any constraint on non-consumed compounds.

A particular solution is then selected from the solution space using an objective function that identifies a metric that is to be maximized or minimized. For example, the objective function may be defined to indicate that biomass growth is to be maximized and may identify relative availability quantities across multiple metabolites that correspond to a biomass representation. The possible solutions can be identified using stoichiometry defined for each reaction and linear programming. Thus, for each of a set of metabolites, the simulation may calculate an availability of the metabolite based on extent to which it is being consumed and/or produced by one or more reactions.

The network can further be configured to include multiple other modules to represent replication, transcription and translation actions. Replication can be simulated using a bulk mass-flow model. Transcription and translation can each be simulated using a bulk mass-flow model. At each time point, a cross-module data structure can be updated based on results from each model, such that the module results are synthesized. Each module can then retrieve select values from the cross-module data structure to use for processing at a next time step.

The left three graphs illustrate availability levels in a simulation of a wild type of a cell. The right three graphs illustrate availability levels in a simulation of a cell having a knockout of gene NWMN_RS06600. A result of this knock out is that undecaprenyl is not synthesized. Initial values for the simulation nonetheless identified presence of some undecaprenyl, though no additional undecaprenyl can be produced.

Each of the graphs show an amount (as a count) of different molecules over a four-generation simulation run. Each generation is completed when a cell-division event is detected. The top graphs show availalability of undecaprenyl-phosphate (bottom line) and undecaprenyl-diphosphate (top line). Both forms are shown in the graph, as the simulated cell can perform reactions that cause the cofactor to switch between these states, even when the knockout is in place to preclude synthesis of the cofactor.

With respect to the wild type, the level of each form of the cofactor grows to each cell division. With respect to the knockout, the undecaprenyl-phosphate is converted to undecaprenyl-diphosphate at the beginning of the simulation but then it is diluted out through the next generations. More specifically, the availability of undecaprenyl-diphosphate drops by 50% after each cell division.

The middle-row and bottom-row graphs show how the availability of peptidoglycan and WTA change across the simulation time period. As noted above, each of these compounds are products of reaction series that use undecaprenyl. As shown, the availability of these products are the same irrespective of whether the knockout was simulated. This occurs because the undecaprenyl is not consumed during the reaction series used to produce peptidoglycan or WTA.

Figure 11:
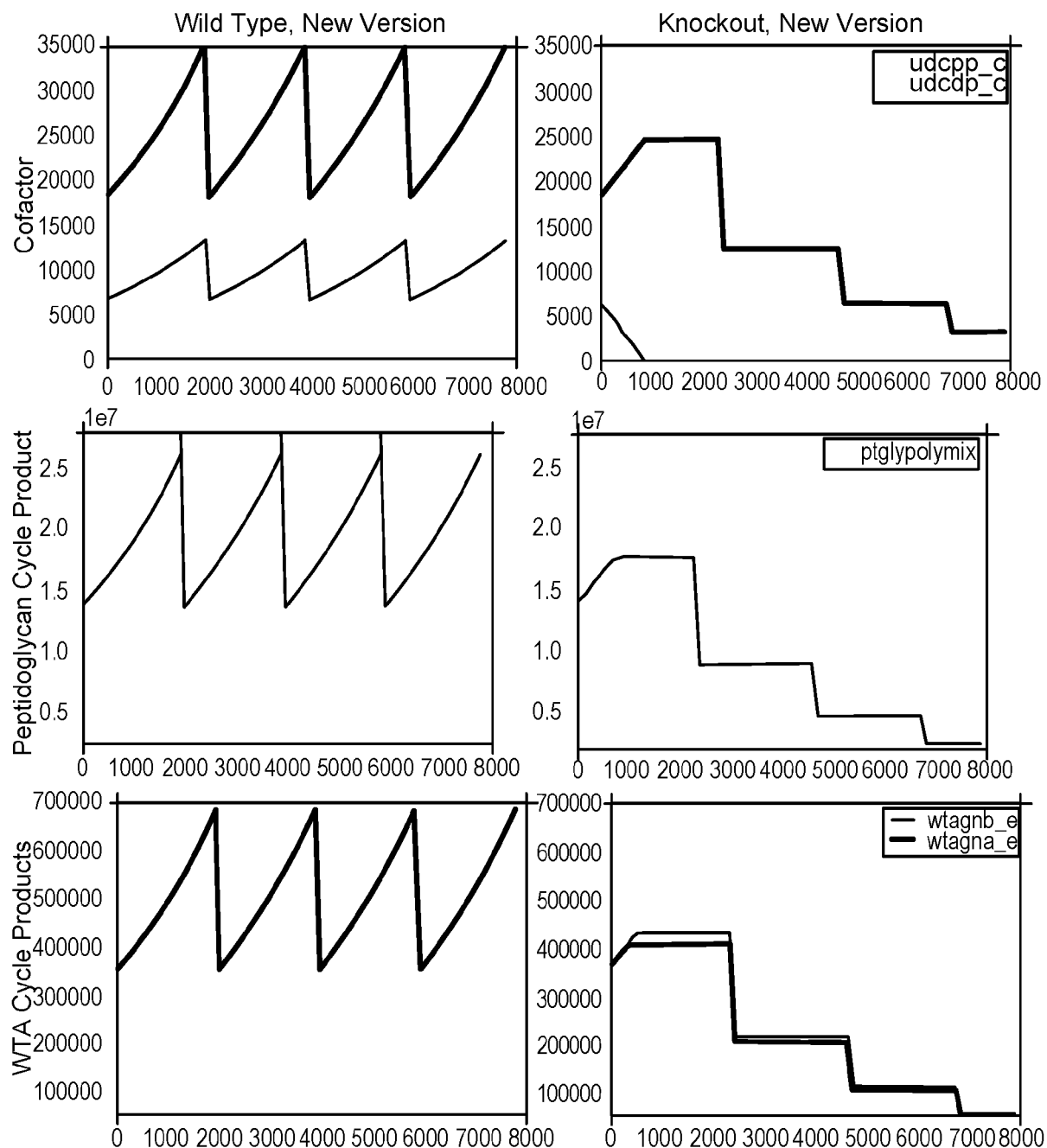
FIG. 11 shows examples of dynamics of components of a simulated network when constraints on reusable components are used.

FIG. 11 shows examples of dynamics of components of a simulated network when constraints on reusable components are used. The configuration of the network is the same as the configuration of the network used to produce the graphs of FIG. 10 except that a constraint is imposed that indicates that an availability of undecaprenyl must be greater than or equal to a sum of a first product of a sequestration duration of the peptidoglycan reaction series and the flux of the peptidoglycan reaction series and a second product of a sequestration duration of the WTA reaction series and the flux of the WTA reaction series.

The top graphs, showing the dynamics of undecaprenyl, are the same as those shown in FIG. 10. However, the cycle-product graphs for the knockout differ from the corresponding graphs in FIG. 10. In the constraint-integrated simulation, the availability of both the peptiglycan cycle product and the WTA cycle product decrease over generations. More specifically, after each cell division, the cycle products drop by half after each cell division, following the pattern of undecaprenyl diphosphate. Thus, the constraint caused the reduced prevalence of the cofactor in the knockout to also cause a reduction in the flux of the cofactor-supported reaction series.

Thus, the added constraint improves the accuracy of the simulation. Importantly, the accuracy improvement includes improving the accuracy of the interplay between availability of different compounds. Accurately simulating this dependency can improve the ability by which the simulation can accurately estimate the effect of (for example) a pharmaceutical, a mutation and/or an environment. Output from the simulation can be provided to (for example) one or more user devices, drug-screening systems, and/or treatment-provision systems. Thus, improved accuracy of the simulation can improve the quality of developing and/or selecting effective treatments.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/ or data.

While the principles of the disclosure have been described above in connection with specific apparatuses and methods, it is to be clearly understood that this description is made only by way of example and not as limitation on the scope of the disclosure.

What is claimed is:

1. A system for simulating networks using dynamics-based constraints, the system comprising:
    one or more data processors; and
    a non-transitory computer readable storage medium containing instructions which, when executed on the one or more data processors, cause the one or more data processors to perform actions including:
        receiving input that indicates a set of reactions representative of activity of a biological network, each reaction of the set of reactions identifying stoichiometry indicative of relative quantities of metabolites being consumed and produced by the reaction;
        identifying, based on the set of reactions, a metabolite that is reused across cycles of at least one reaction of the set of reactions;
        defining a constraint on a quantity of the metabolite based on one or more characteristics of the reuse of the metabolite across cycles of the at least one reaction; and
        executing a simulation using the set of reactions and the constraint, wherein execution of the simulation generates one or more simulation outputs.

2. The system of claim 1, wherein the actions further include:
    identifying a use rate indicative of a quantity of the cycles of the at least one reaction performed per unit of time; and
    identifying a per-cycle duration of the at least one reaction;
    wherein the one or more characteristics of the reuse of the metabolite include the use rate and the per-cycle duration.

3. The system of claim 1, wherein the set of reactions is a first set of reactions and the at least one reaction includes a second set of reactions, wherein a first reaction of the second set of reactions consumes the metabolite, and a later reaction of the second set of reactions releases the metabolite.

4. The system for simulating networks using dynamics-based constraints of claim 1, wherein the actions further include:
    determining that the metabolite is further reused across other cycles of another at least one reaction;
    wherein the constraint on the quantity of the metabolite is defined further based on one or more other characteristics of the reuse of the metabolite across other cycles of the other at least one reaction.

5. The system for simulating networks using dynamics-based constraints of claim 4, wherein the constraint is defined to indicate that the quantity of the metabolite is to remain to be at least equal to a sum of multiple product values, the multiple product values including:
    a first product of a first use rate and a first duration corresponding to the at least one reaction; and
    a second product of a second use rate and a second duration corresponding to the other at least one reaction.

6. The system for simulating networks using dynamics-based constraints of claim 1, wherein the biological network is comprised by a cell, and wherein the metabolite is a cofactor, enzyme or ribosome.

7. The system for simulating networks using dynamics-based constraints of claim 1, wherein executing the simulation includes identifying, for each reaction of the set of reactions, a flux of the reaction based on an objective function that is defined based on the stoichiometries of the set of reactions.

8. The system for simulating networks using dynamics-based constraints of claim 1, wherein the one or more simulation outputs include time-course data indicating dynamics of at least part of the network.

9. The system for simulating networks using dynamics-based constraints of claim 1, wherein executing the simulation includes using linear programming.

10. A computer-implemented method comprising:
    receiving input that indicates a set of reactions representative of activity of a biological network, each reaction of the set of reactions identifying stoichiometry indicative of relative quantities of metabolites being consumed and produced by the reaction;
    identifying, based on the set of reactions, a metabolite that is reused across cycles of at least one reaction of the set of reactions;
    defining a constraint on a quantity of the metabolite based on one or more characteristics of the reuse of the metabolite across cycles of the at least one reaction; and
    executing a simulation using the set of reactions and the constraint, wherein execution of the simulation generates one or more simulation outputs.

11. The method for simulating networks using dynamics-based constraints of claim 10, further comprising:
    identifying a use rate indicative of a quantity of the cycles of the at least one reaction performed per unit of time; and
    identifying a per-cycle duration of the at least one reaction;
    wherein the one or more characteristics of the reuse of the metabolite include the use rate and the per-cycle duration.

12. The method for simulating networks using dynamics-based constraints of claim 10, wherein the set of reactions in a first set of reactions and the at least one reaction includes a second set of reactions, wherein a first reaction of the second set of reactions consumes the metabolite, and a later reaction of the second set of reactions releases the metabolite.

13. The method for simulating networks using dynamics-based constraints of claim 10, further comprising:
    determining that the metabolite is further reused across other cycles of another at least one reaction;
    wherein the constraint on the quantity of the metabolite is defined further based on one or more other characteristics of the reuse of the metabolite across other cycles of the other at least one reaction.

14. The method for simulating networks using dynamics-based constraints of claim 13, wherein the constraint is defined to indicate that the quantity of the metabolite is to remain to be at least equal to a sum of multiple product values, the multiple product values including:
    a first product of a first use rate and a first duration corresponding to the at least one reaction; and a second product of a second use rate and a second duration corresponding to the other at least one reaction.

15. The method for simulating networks using dynamics-based constraints of claim 10, wherein the biological network is comprised by a cell, and wherein the metabolite is a cofactor, enzyme or ribosome.

16. The method for simulating networks using dynamics-based constraints of claim 10, wherein executing the simulation includes identifying, for each reaction of the set of reactions, a flux of the reaction based on an objective function that is defined based on the stoichiometries of the set of reactions.

17. The method for simulating networks using dynamics-based constraints of claim 10, wherein the one or more simulation outputs include time-course data indicating dynamics of at least part of the network.

18. The method for simulating networks using dynamics-based constraints of claim 10, wherein executing the simulation includes using linear programming.

19. A computer-program product tangibly embodied in a non-transitory machine-readable storage medium, including instructions configured to cause one or more data processors to perform actions including:
   receiving input that indicates a set of reactions representative of activity of a biological network, each reaction of the set of reactions identifying stoichiometry indicative of relative quantities of metabolites being consumed and produced by the reaction;
   identifying, based on the set of reactions, a metabolite that is reused across cycles of at least one reaction of the set of reactions;
   defining a constraint on a quantity of the metabolite based on one or more characteristics of the reuse of the metabolite across cycles of the at least one reaction; and
   executing a simulation using the set of reactions and the constraint, wherein execution of the simulation generates one or more simulation outputs.

20. The computer-program product of claim 19, wherein the actions further include:
   identifying a use rate indicative of a quantity of the cycles of the at least one reaction performed per unit of time; and
   identifying a per-cycle duration of the at least one reaction;
   wherein the one or more characteristics of the reuse of the metabolite include the use rate and the per-cycle duration.

21. The computer-program product of claim 19, wherein the set of reactions is a first set of reactions and the at least one reaction includes a second set of reactions, wherein a first reaction of the second set of reactions consumes the metabolite, and a later reaction of the second set of reactions releases the metabolite.

22. The computer-program product of claim 21, wherein the actions further include:
   determining that the metabolite is further reused across other cycles of another at least one reaction;
   wherein the constraint on the quantity of the metabolite is defined further based on one or more other characteristics of the reuse of the metabolite across other cycles of the other at least one reaction.

23. The computer-program product of claim 19, wherein the constraint is defined to indicate that the quantity of the metabolite is to remain to be at least equal to a sum of multiple product values, the multiple product values including:
   a first product of a first use rate and a first duration corresponding to the at least one reaction; and
   a second product of a second use rate and a second duration corresponding to the other at least one reaction.

24. The computer-program product of claim 19, wherein the biological network is comprised by a cell, and wherein the metabolite is a cofactor, enzyme or ribosome.

25. The computer-program product of claim 19, wherein executing the simulation includes identifying, for each reaction of the set of reactions, a flux of the reaction based on an objective function that is defined based on the stoichiometries of the set of reactions.

26. The computer-program product of claim 19, wherein the one or more simulation outputs include time-course data indicating dynamics of at least part of the network.

* * * * *